(12) United States Patent
Stern et al.

(10) Patent No.: US 6,673,574 B2
(45) Date of Patent: Jan. 6, 2004

(54) ORAL DELIVERY OF PEPTIDES USING ENZYME-CLEAVABLE MEMBRANE TRANSLOCATORS

(75) Inventors: William Stern, Tenafly, NJ (US); Nozer M. Mehta, Randolph, NJ (US); Martha V. L. Ray, Nutley, NJ (US)

(73) Assignee: Unigene Laboratories Inc., Fairfield, NJ (US)

(*) Notice: Subject to any disclaimer, the term of this patent is extended or adjusted under 35 U.S.C. 154(b) by 0 days.

(21) Appl. No.: 09/997,465

(22) Filed: Nov. 29, 2001

(65) Prior Publication Data

US 2003/0118610 A1 Jun. 26, 2003

Related U.S. Application Data

(60) Provisional application No. 60/250,055, filed on Nov. 30, 2000.

(51) Int. Cl.[7] ............ C12P 21/04; C12P 21/08; C12N 9/00; A61K 39/38; A61K 39/00
(52) U.S. Cl. ............ 435/69.7; 435/183; 530/387.3; 424/184.1; 424/192.1; 424/193.1
(58) Field of Search ................ 435/69.7, 183; 530/387.3; 424/184.1, 192.1, 193.1

(56) References Cited

U.S. PATENT DOCUMENTS 5,766,620 A    6/1998   Heiber et al. ............... 424/436
5,968,895 A   10/1999   Gefter et al. ................. 514/2
6,248,558 B1   6/2001   Lin et al. .................. 435/69.1

FOREIGN PATENT DOCUMENTS

WO     WO0144199     6/2001

OTHER PUBLICATIONS

T. Fernandez et al., "Ferrying Proteins to the Other Side," Nature Biotechnology 16:418–420 (May 1998).
A. Bernkop–Schnurch, "The Use of Inhibitory Agents to Overcome the Enzymatic Barrier to Perorally Administered Therapeutic Peptides and Proteins," Journal of Controlled Release 52:1–16 (1998).
D. Patel et al., "Peptide Targeting and Delivery Across the Blood–Brain Barrier Utilizing Synthetic Triglyceride Esters: Design, Synthesis, and Bioactivity," Bioconjugate Chem. 8:434–441 (1997).

*Primary Examiner*—Hankyel T. Park
(74) *Attorney, Agent, or Firm*—Ostrolenk, Faber, Gerb & Soffen, LLP

(57) ABSTRACT

Bioavailability of peptide active agents to be administered orally is enhanced by a pharmaceutical composition providing targeted release of the peptide to the intestine in addition to having the active peptide linked to a membrane translocator which is capable of being at least partially cleaved in vivo by an enzyme. The composition includes an acid-resistant protective vehicle which transports components of the invention through the stomach and a sufficient amount of a pH-lowering agent to lower local intestinal pH. All components are released together into the intestine with the peptide.

57 Claims, 8 Drawing Sheets

SEQUENCE LISTING

```
<160> NUMBER OF SEQ ID NOS: 22

<210> SEQ ID NO 1
<211> LENGTH: 26
<212> TYPE: PRT
<213> ORGANISM: Homo sapiens

<400> SEQUENCE: 1

Ala Ala Val Ala Leu Leu Pro Ala Val Leu Leu Ala Leu Leu Ala Pro
1               5                   10                  15

Val Asn Arg Lys Arg Asn Lys Leu Met Pro
            20                  25

<210> SEQ ID NO 2
<211> LENGTH: 11
<212> TYPE: PRT
<213> ORGANISM: Human immunodeficiency virus type 1

<400> SEQUENCE: 2

Tyr Gly Arg Lys Lys Arg Arg Gln Arg Arg Arg
1               5                   10

<210> SEQ ID NO 3
<211> LENGTH: 15
<212> TYPE: PRT
<213> ORGANISM: Homo sapiens

<400> SEQUENCE: 3

Val Thr Val Leu Ala Leu Gly Ala Leu Ala Gly Val Gly Val Gly
1               5                   10                  15

<210> SEQ ID NO 4
<211> LENGTH: 12
<212> TYPE: PRT
<213> ORGANISM: Homo sapiens

<400> SEQUENCE: 4

Ala Ala Val Leu Leu Pro Val Leu Leu Ala Ala Pro
1               5                   10

<210> SEQ ID NO 5
<211> LENGTH: 5
<212> TYPE: PRT
<213> ORGANISM: Artificial Sequence
<220> FEATURE:
```

<223> OTHER INFORMATION: Synthetic Construct
<220> FEATURE:
<221> NAME/KEY: MISC_FEATURE
<222> LOCATION: (5)..(5)
<223> OTHER INFORMATION: "Xaa" means any amino acid

<400> SEQUENCE: 5

Tyr Val Ala Asp Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(3)
<223> OTHER INFORMATION: "Xaa" means any amino acid
<220> FEATURE:
<221> NAME/KEY: MISC_FEATURE
<222> LOCATION: (5)..(5)
<223> OTHER INFORMATION: "Xaa" means any amino acid

<400> SEQUENCE: 6

Asp Xaa Xaa Asp Xaa
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(7)
<223> OTHER INFORMATION: 2 or 4 "Xaa" may be missing and when present,
      "Xaa" means any amino acid
<220> FEATURE:
<221> NAME/KEY: MISC_FEATURE
<222> LOCATION: (9)..(9)
<223> OTHER INFORMATION: "Xaa" means any amino acid

<400> SEQUENCE: 7

Arg Xaa Xaa Xaa Xaa Xaa Xaa Arg Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(7)
<223> OTHER INFORMATION: 2 or 4 "Xaa" may be missing and when present,
      "Xaa" means any amino acid
<220> FEATURE:
<221> NAME/KEY: MISC_FEATURE
<222> LOCATION: (9)..(9)
<223> OTHER INFORMATION: "Xaa" means any amino acid

<400> SEQUENCE: 8

Lys Xaa Xaa Xaa Xaa Xaa Xaa Arg Xaa
1               5

<210> SEQ ID NO 9
<211> LENGTH: 5

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: "Xaa" means any amino acid

<400> SEQUENCE: 9

Arg Thr Lys Arg Xaa
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: "Xaa" means any amino acid

<400> SEQUENCE: 10

Arg Val Arg Arg Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: "Xaa" means any amino acid

<400> SEQUENCE: 11

Arg Val Arg Arg Xaa
      1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: "Xaa" means any amino acid

<400> SEQUENCE: 12

Trp Val Pro Xaa
1

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: "Xaa" means any amino acid

<400> SEQUENCE: 13
```

Trp Val Ala Xaa
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: "Xaa" means any amino acid
<220> FEATURE:
<221> NAME/KEY: MISC_FEATURE
<222> LOCATION: (3)..(4)
<223> OTHER INFORMATION: "Xaa" means any amino acid

<400> SEQUENCE: 14

Xaa Phe Xaa Xaa
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: "Xaa" means any amino acid
<220> FEATURE:
<221> NAME/KEY: MISC_FEATURE
<222> LOCATION: (3)..(4)
<223> OTHER INFORMATION: "Xaa" means any amino acid

<400> SEQUENCE: 15

Xaa Tyr Xaa Xaa
1

<210> SEQ ID NO 16
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: "Xaa" means any amino acid
<220> FEATURE:
<221> NAME/KEY: MISC_FEATURE
<222> LOCATION: (3)..(4)
<223> OTHER INFORMATION: "Xaa" means any amino acid

<400> SEQUENCE: 16

Xaa Trp Xaa Xaa
1

<210> SEQ ID NO 17
<211> LENGTH: 12
<212> TYPE: PRT
<213> ORGANISM: Artificial Sequence
<220> FEATURE:
<223> OTHER INFORMATION: Synthetic Construct

<400> SEQUENCE: 17

Asp Arg Tyr Ile Pro Phe His Leu Leu Val Tyr Ser
1               5                   10

```
<210> SEQ ID NO 18
<211> LENGTH: 11
<212> TYPE: PRT
<213> ORGANISM: Human immunodeficiency virus type 1

<400> SEQUENCE: 18

Trp Gly Arg Lys Lys Arg Arg Gln Arg Arg Arg
1               5                   10

<210> SEQ ID NO 19
<211> LENGTH: 33
<212> TYPE: PRT
<213> ORGANISM: Oncorhynchus keta

<400> SEQUENCE: 19

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

Gly

<210> SEQ ID NO 20
<211> LENGTH: 57
<212> TYPE: DNA
<213> ORGANISM: Artificial Sequence
<220> FEATURE:
<223> OTHER INFORMATION: Synthetic Construct

<400> SEQUENCE: 20
cctacggtcg taaaaaacgt cgtcagcgtc gtcgttgggt tgcgtgttct aacttgt        57

<210> SEQ ID NO 21
<211> LENGTH: 59
<212> TYPE: DNA
<213> ORGANISM: Artificial Sequence
<220> FEATURE:
<223> OTHER INFORMATION: Synthetic Construct

<400> SEQUENCE: 21
agacaagtta gaacacgcaa cccaacgacg acgctgacga cgttttttac gaccgtagg     59

<210> SEQ ID NO 22
<211> LENGTH: 4
<212> TYPE: PRT
<213> ORGANISM: Artificial Sequence
<220> FEATURE:
<223> OTHER INFORMATION: Synthetic Construct

<400> SEQUENCE: 22

Cys Ser Asn Leu
1
```

ORAL DELIVERY OF PEPTIDES USING ENZYME-CLEAVABLE MEMBRANE TRANSLOCATORS

RELATED APPLICATION

This application is a continuation-in-part of co-pending provisional U.S. patent application Ser. No. 60/250,055 filed Nov. 30, 2000.

BACKGROUND OF THE INVENTION

1. Field of the Invention

The present invention relates to oral peptide pharmaceuticals where the active compounds include a plurality of amino acids and at least one peptide bond in their molecular structures, and to methods of enhancing bioavailability of such peptide active compounds when administered orally.

2. Description of the Related Art

Numerous human hormones, neurotransmitters and other important biological compounds have peptides as a substantial part of their molecular structures. Many diseases respond positively to raising the level of these peptide compounds in patients. Therapeutically effective amounts of such biologically relevant peptides may be administered to patients in a variety of ways. However, as discussed further below, preferred oral administration is very difficult with this type of active compound.

Salmon calcitonin, for example, is a peptide hormone which decreases calcium release from bone. When used to treat bone-related diseases and calcium disorders (such as osteoporosis, Paget's disease, hypercalcemia of malignancy, and the like), it has the effect of helping maintain bone density. Many types of calcitonin have been isolated (human calcitonin, salmon calcitonin, eel calcitonin, elkatonin, porcine calcitonin, and chicken calcitonin). There is significant structural non-homology among the various calcitonin types. For example, there is only 50% percent identity between the amino acids making up human calcitonin and those making up salmon calcitonin. Notwithstanding the difference in molecular structure, salmon calcitonin may be used in the human treatment of the calcitonin-responsive diseases discussed above.

Peptide pharmaceuticals used in the prior art frequently have been administered by injection or by nasal administration. Insulin is one example of a peptide pharmaceutical frequently administered by injection. A more preferred oral administration tends to be problematic because peptide active compounds are very susceptible to degradation in the stomach and intestines. For example, while the prior art has reported an ability to achieve reproducible blood levels of salmon calcitonin when administered orally, these levels are low. This is believed to be because salmon calcitonin lacks sufficient stability in the gastrointestinal tract, and tends to be poorly transported through intestinal walls into the blood. However, injection and nasal administration are significantly less convenient than, and involve more patient discomfort than, oral administration. Often this inconvenience or discomfort results in substantial patient noncompliance with a treatment regimen. Thus, there is a need in the art for more effective and reproducible oral administration of peptide pharmaceuticals like insulin, salmon calcitonin and others discussed in more detail herein.

Proteolytic enzymes of both the stomach and intestines may degrade peptides, rendering them inactive before they can be absorbed into the bloodstream. Any amount of peptide that survives proteolytic degradation by proteases of the stomach (typically having acidic pH optima) is later confronted with proteases of the small intestine and enzymes secreted by the pancreas (typically having neutral to basic pH optima). Specific difficulties arising from the oral administration of a peptide like salmon calcitonin involve the relatively large size of the molecule, and the charge distribution it carries. This may make it more difficult for salmon calcitonin to penetrate the mucus along intestinal walls or to cross the intestinal brush border membrane into the blood.

Normally, the plasma membrane of eukaryotic cells is impermeable to large peptides or proteins. However, certain hydrophobic amino acid sequences, variously called as ferry peptides or membrane translocating sequences, when fused to the N- or C-terminus of functional proteins, can act as membrane translocators, and mediate the transport of these proteins into living cells. This method of protein delivery into cells, while potentially very useful, has two main drawbacks. First, the protein cannot be targeted to any specific cell type. Therefore, once it is injected and enters the circulation, it will presumably enter all cell types in a non-specific, non-receptor mediated manner. This would cause a huge dilution effect, such that very high concentrations of the protein need to be injected in order to achieve an effective concentration in the target cell type. Also, the protein could be extremely toxic when it enters cells in non-target tissues. A third drawback is that the continued presence of the ferry peptide could make the protein very antigenic, and could also interfere with its biological activity. These above drawbacks would apply whether the fusion was delivered by injection or nasal or oral route.

SUMMARY OF THE INVENTION

It is accordingly an object of the present invention to provide a therapeutically effective oral pharmaceutical composition for reliably delivering pharmaceutical peptides, e.g., physiologically active peptide agents such as insulin, salmon calcitonin, vasopressin and others discussed herein.

It is a further object of the invention to provide therapeutic methods for enhancing the bioavailability of such peptides.

It is a further object of the invention to provide methods of treating bone-related diseases and calcium disorders by administering salmon calcitonin orally.

In one aspect, the invention provides a pharmaceutical composition for oral delivery of a physiologically active peptide agent comprising:

(A) a therapeutically effective amount of said active peptide linked to a membrane translocator, said membrane translocator is capable of being at least partially cleaved by a blood or lymphatic system protease;

(B) at least one pharmaceutically acceptable pH-lowering agent and/or protease inhibitor; and (C) an acid resistant protective vehicle effective to transport said pharmaceutical composition through the stomach of a patient while preventing contact between said active peptide agent and stomach proteases.

Preferred peptide active agents include but are not limited to insulin, vasopressin salmon calcitonin, glucagon-like peptide 1, parathyroid hormone, luteinizing hormone releasing hormone, erythropoeitin, and analogs thereof. Especially preferred is salmon calcitonin.

In another aspect, the invention provides a method for enhancing the bioavailability of a therapeutic peptide active agent delivered orally, said method comprising:

(A) linking said peptide agent to a membrane translocator capable of being at least partially cleaved by a plasma protease; and (B) selectively releasing said peptide active agent linked to said membrane translocator, together with at least one pH-lowering agent and/or protease inhibitor into a patient's intestine following passage of said peptide active agent, pH-lowering agent and/or protease inhibitor through said patient's mouth and stomach under protection of an acid resistant protective vehicle which substantially prevents contact between stomach proteases and said peptide agent.

The present invention is believed to reduce the likelihood of proteolytic degradation of the peptide active compound by simultaneously protecting the peptide from proteolytic attack by (1) stomach proteases which are typically most active at acidic pHs and (2) intestinal or pancreatic proteases (which are typically most active at basic to neutral pH).

Then the invention is believed to promote the process by which the peptide crosses the intestinal brush border membrane into the blood due to the presence of the membrane translocator, while continuing to protect the peptide from proteolytic degradation.

An acid resistant protective vehicle protects the peptide active agent from the acid-acting proteases of the stomach. Significant quantities of acid (with which the peptide active agent is intermixed) then reduce the activity of neutral to basic-acting proteases in the intestine (e.g., luminal or digestive protease and proteases of the brush border membrane) by lowering pH below the optimal activity range of these intestinal proteases.

The membrane translocator capable when linked to the active peptide agent enhances transport of the peptide agent through intestinal mucous layers, through the brush border membrane and into the blood. Subsequently, the membrane translocator is cleaved by a blood or lymphatic system protease, thus releasing the active peptide agent in a patient's system.

Other features and advantages of the present invention will become apparent from the following detailed description of the invention.

| Lane 1 | Total lysate material sample = negative control |
| Lane 2 | BioRad Precision ™ Standards; |
| Lane 3 | Insoluble cell lysate material (purified recombinant OmpA-MT3-sCTgly), input to purification; |
| Lane 4 | Analytical RP analysis of solubilization; |
| Lane 5 | Preparative purification sample post solubilization, 4 uL; |
| Lane 6 | Preparative purification sample post solubilization, 1.5 uL; and |
| Lane 7 | GST-sCTgly standard = positive control. |

Figure 8:
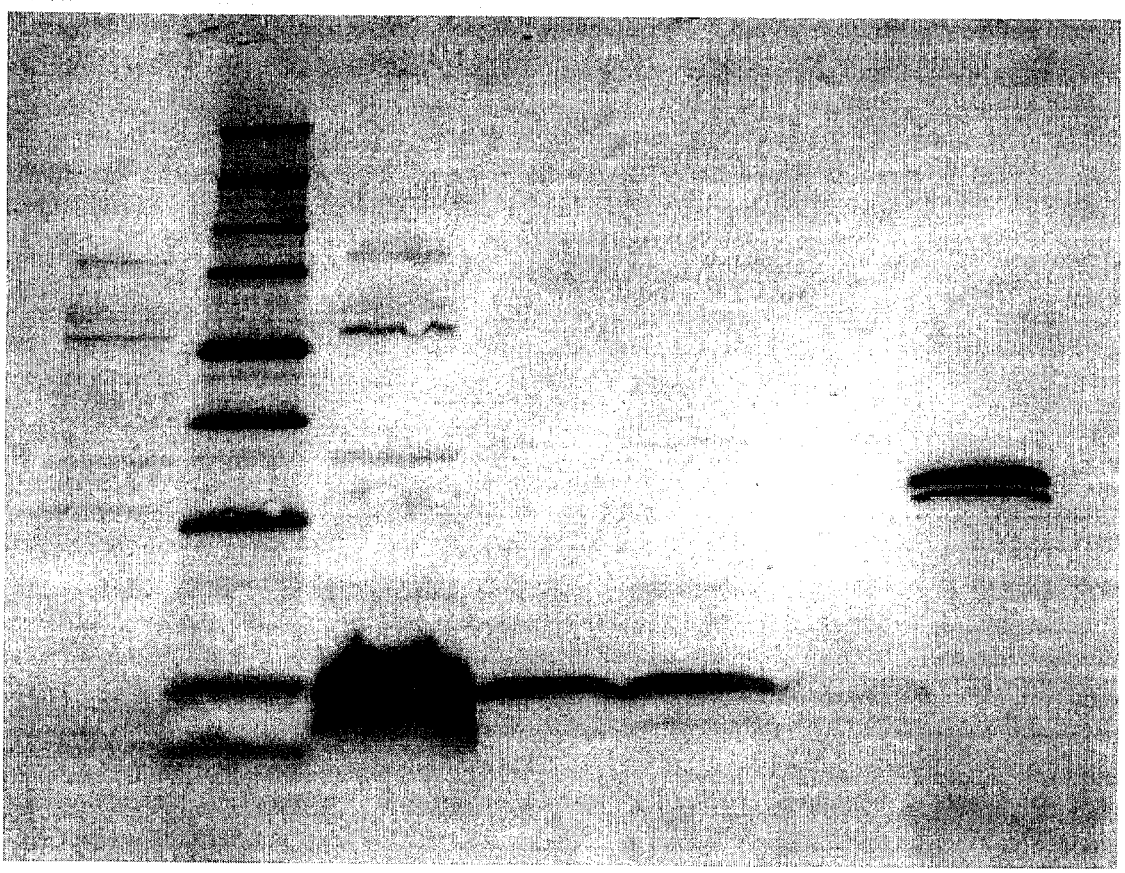

FIG. 8 shows a standard western blotting using the sCT-specific antibody for the following samples:

| Lane 1 | Total lysate material sample = negative control |
| Lane 2 | BioRad Precision ™ Standards; |
| Lane 3 | Insoluble cell lysate material (purified recombinant OmpA-MT3-sCTgly), input to purification; |
| Lane 4 | Analytical RP analysis of solubilization; |
| Lane 5 | Preparative purification sample post solubilization, 4 uL; |
| Lane 6 | Preparative purification sample post solubilization, 1.5 uL; and |
| Lane 7 | GST-sCTgly standard = positive control. |

DETAILED DESCRIPTION OF THE INVENTION

In accordance with the invention, patients in need of treatment with peptide active ingredients are provided with an oral pharmaceutical composition thereof (at appropriate dosage), preferably but not necessarily in tablet or capsule form of an ordinary size in the pharmaceutical industry. The dosages and frequency of administering the products are discussed in more detail below. Patients who may benefit are any who suffer from disorders that respond favorably to increased levels of a peptide-containing compound. For example, oral salmon calcitonin in accordance with the invention may be used to treat patients who suffer from calcium disorders or bone diseases. The invention may be used, for example, to treat osteoporosis, Paget's disease, hypercalcemia of malignancy and the like, with oral calcitonin, preferably salmon calcitonin.

Salmon calcitonin is a preferred active ingredient for use in accordance with the invention for a number of reasons. For example, it provides a number of advantages over even human calcitonin, even though used as a pharmaceutical agent for human patients. Among the advantages provided by utilizing salmon calcitonin instead of human calcitonin for the treatment of human osteoporosis are increased potency, analgesia and increased half-life. Salmon calcitonin is more effective than natural human calcitonin in treatment, since lower dosages are necessary than with human calcitonin. There is substantial non-homology between salmon and human calcitonin, with only 50% identity in the amino acid sequences of the two calcitonins.

Salmon calcitonin enjoys an unexpectedly higher bioavailability when administered orally in accordance with the present invention than would be expected for its molecular weight. In an oral formulation, the bioavailability of salmon calcitonin when linked to a membrane translocator (MT) according to the invention is significantly increased.

Without intending to be bound by theory, the pharmaceutical composition of the invention is believed to overcome a series of different and unrelated natural barriers to bioavailability. Various components of the pharmaceutical compositions act to overcome different barriers by mechanisms appropriate to each, and result in synergistic effects on the bioavailability of a peptide active ingredient.

The peptide active compound may be administered orally. In accordance with the invention, the presence of at least one MT, preferably two MTs, more preferably, two peptide MTs would enhance the membrane permeability of the fusion peptide across the lumen of the intestine and provide for improved bioavailability. Since the MT link to the active peptide can be cleaved by an enzyme in the blood or the lymphatic system, thereby leaving the active peptide free to reach its target.

Also, in accordance with the invention, proteolytic degradation of the peptide and of the membrane translocator by stomach enzymes (most of which are active in the acid pH range) and intestinal or pancreatic proteases (most of which are active in the neutral to basic pH range) is reduced.

Again, without intending to be bound by theory, it appears that, in accordance with the present invention, the peptide is transported through the stomach under the protection of an appropriate acid-resistant protective vehicle for substantially preventing contact between the salmon calcitonin or other active peptide and any stomach proteases capable of degrading it. Once the pharmaceutical composition of the invention passes through the stomach and enters the intestinal region where basic to neutral pH predominates, and where proteases tend to have basic to neutral pH optima, the enteric coating or other vehicle releases the peptide and acid or protease inhibitors (in close proximity to each other).

The acid is believed to lower the local intestinal pH (where the active agent has been released) to levels below the optimal range for many intestinal proteases and other intestinal enzymes. This decrease in pH reduces the proteolytic activity of the intestinal proteases, thus affording protection to the peptide and the membrane translocator from potential degradation. The activity of these proteases is diminished by the temporarily acidic environment provided by the invention. It is preferred that sufficient acid be provided that local intestinal pH is lowered temporarily to 5.5 or below, preferably 4.7 or below and more preferably 3.5 or below. The sodium bicarbonate test described below (in the section captioned "the pH-Lowering Agent") is indicative of the required acid amount. Preferably, conditions of reduced intestinal pH persist for a time period sufficient to protect the peptide agent and the membrane translocator from proteolytic degradation until at least some of the peptide agent has had an opportunity to cross the intestinal wall into the bloodstream. For salmon calcitonin, experiments have demonstrated a $T_{max}$ of 5–15 minutes for blood levels of salmon calcitonin when the active components are injected directly into the duodenum, ileum or colon of rats.

Alternatively, protease inhibitors are believed to reduce the proteolytic activity of the intestinal proteases, thus affording protection to the peptide and the membrane translocator from premature potential degradation.

Compositions of the present invention can optionally contain absorption enhancers. The absorption enhancers of the invention synergistically promote peptide absorption into the blood while conditions of reduced proteolytic activity prevail.

The mechanism by which the invention is believed to accomplish the goal of enhanced bioavailability is aided by having active components of the pharmaceutical composition released together as simultaneously as possible. To this end, it is preferred to keep the volume of enteric coating as low as possible consistent with providing protection from stomach proteases. Thus enteric coating is less likely to interfere with peptide release, or with the release of other components in close time proximity with the peptide. The enteric coating should normally add less than 30% to the weight of the remainder of pharmaceutical composition (i.e., the other components of the composition excluding enteric coating). Preferably, it is less than 20% and, more preferably, the enteric coating adds between 10% and 20% to the weight of the uncoated ingredients.

The absorption enhancer which may be a solubility enhancer and/or transport enhancer (as described in more detail below) aids transport of the peptide agent from the intestine to the blood, and may promote the process so that it better occurs during the time period of reduced intestinal pH and reduced intestinal proteolytic activity. Many surface active agents may act as both solubility enhancers and transport (uptake) enhancers. Again without intending to be bound by theory, it is believed that enhancing solubility provides (1) a more simultaneous release of the active components of the invention into the aqueous portion of the intestine, (2) better solubility of the peptide in, and transport through, a mucous layer along the intestinal walls. Once the peptide active ingredient reaches the intestinal walls, an uptake enhancer provides better transport through the brush border membrane of the intestine into the blood, via either transcellular or paracellular transport. As discussed in more detail below, many preferred compounds may provide both functions. In those instances, preferred embodiments utilizing both of these functions may do so by adding only one additional compound to the pharmaceutical composition. In other embodiments, separate absorption enhancers may provide the two functions separately.

Each of the preferred ingredients of the pharmaceutical composition of the invention is separately discussed below. Combinations of multiple pH-lowering agents, or multiple enhancers can be used as well as using just a single pH-lowering agent and/or single enhancer. Some preferred combinations are also discussed below.

Peptide Active Ingredients

Peptide active ingredients which may benefit from oral delivery in accordance with the invention include any therapeutic agent that is physiologically active and has a plurality of amino acids and at least one peptide bond in its molecular structure. These peptide active ingredients are linked to an MT sequence to facilitate their absorption from the intestine. The MT must be protected from cleavage by proteases in the stomach and intestine before its absorption. However, once absorbed, the MT should be able to be at least partially removed by proteases to free up the active peptide.

The MT can comprise an amino acid sequence, preferably a signal peptide or signal sequence. A "signal peptide," as used herein, is a sequence of amino acids generally but not necessarily of a length of about 10 to about 50 or more amino acid residues, many (typically about 55–60%) residues of which are hydrophobic such that they have a hydrophobic, lipid-soluble portion. The hydrophobic portion is a common, major motif of the signal peptide, and it is often a central part of the signal peptide of protein secreted from cells. A signal peptide is a peptide capable of penetrating through the cell membrane to allow the export of cellular proteins. The signal peptides of this invention, as discovered herein, are also "importation competent," i.e., capable of penetrating through the cell membrane from outside the cell to the interior of the cell. The amino acid residues can be mutated and/or modified (i.e., to form mimetics) so long as the modifications do not affect the translocation-mediating function of the peptide. Thus the word "peptide" includes mimetics and the word "amino acid" includes modified amino acids, as used herein, unusual amino acids, and D-form amino acids. All importation competent signal peptides encompassed by this invention have the function of mediating translocation across a cell membrane from outside the cell to the interior of the cell. They may also retain their ability to allow the export of a protein from the cell into the external milieu. A putative signal peptide can easily be tested for this importation activity following the teachings provided herein, including testing for specificity for any selected cell type.

The following table 1 exemplifies amino acid sequences, each of which can be used as an MT.

TABLE 1

Amino Acid Sequences of Some MT Peptides and Their Sources

| SEQUENCE | SEQUENCE DERIVATION | SOURCE |
| --- | --- | --- |
| ALA-ALA-VAL-ALA-LEU-LEU-PRO-ALA-VAL-LEU-LEU-ALA-LEU-LEU-ALA-PRO-VAL-ASN-ARG-LYS-ARG-ASN-LYS-LEU-MET-PRO (SEQ ID No.1) | Signal Peptide from Kaposi Fibroblast Growth Factor | U.S. Pat. No. 5,807,746 |
| TYR-GLY-ARG-LYS-LYS-ARG-ARG-GLN-ARG-ARG-ARG (SEQ ID No.2) | Protein Transduction Domain of HIV TAT Protein | Schwarz et al. (1999), Science 285:1569 |
| VAL-THR-VAL-LEU-ALA-LEU-GLY-ALA-LEU-ALA-GLY-VAL-GLY-VAL-GLY (SEQ ID No.3) | Signal Sequence of Human Integrin β₃ | Zhang et al. (1988) PNAS 95: 9184 |
| 38 kDa Protein | HSV-VP22 Protein | Phelan et al. (1998), Nature Biotechnology 16:440 |
| ALA-ALA-VAL-LEU-LEU-PRO-VAL-LEU-LEU-ALA-ALA-PRO (SEQ ID No.4) | Modified from 16-residue hydrophobic region of signal sequence of Kaposi fibroblast growth factor. | Rojas et al (1998) Nature Biotechnology 16:370 |

The MT can also comprise fatty acids and/or bile acids. Such molecules, when used, are linked to the active peptide by an amino acid bridge which is subject to cleavage by proteases in the plasma. Alternatively, the MT can be linked to the active peptide by a non-peptidyl linkage, in which case the in vivo enzyme that cleaves the linkage may be an enzyme other than protease. The amino acid bridge must be a target for cleavage by at least one plasma protease. Plasma proteases as well as their target sequences are well known in the art. Table 2 illustrates some of these enzymes as well as their specific targets

TABLE 2

Plasma Proteases and their Specific Targets

| PROTEASE | SPECIFIC TARGET | REMARKS |
| --- | --- | --- |
| Caspase-1 | Tyr-Val-Ala-Asp-Xaa* (SEQ ID No. 5) | |
| Caspase-3 | Asp-Xaa-Xaa-Asp-Xaa (SEQ ID No. 6) | |
| Proprotein convertase 1 | Arg- (Xaa)ₙ -Arg-Xaa (SEQ ID No. 7) | n = 2, 4 or 6 |
| | Lys- (Xaa)ₙ -Arg-Xaa (SEQ ID No. 8) | n = 2, 4, or 6 |

TABLE 2-continued

Plasma Proteases and their Specific Targets

| PROTEASE | SPECIFIC TARGET | REMARKS |
| --- | --- | --- |
| Proprotein convertase 2 | Arg-Arg-Xaa Lys-Arg-Xaa | same as proprotein convertase 1 |
| Proprotein convertase 4 | Glp-Arg-Thr-Lys-Arg-Xaa (SEQ ID No. 9) | |
| Proprotein convertase 4 PACE 4 | Arg-Val-Arg-Arg-Xaa (SEQ ID No. 10) Decanoyl-Arg-Val-Arg-Arg-Xaa (SEQ ID No. 11) | |
| Prolyl oligopeptidase | Pro-Xaa | |
| Endothelin cleaving enzyme followed by dipeptidyl-peptidase IV | Trp-Val-Pro-Xaa (SEQ ID No. 12) Trp-Val-Ala-Xaa (SEQ ID No. 13) | |
| Signal peptidase | | depends on nearby amino acid |
| Neprilysin followed by dipeptidyl-peptidase IV | Xaa-Phe-Yaa-Xaa (SEQ ID No. 14) Xaa-Tyr-Yaa-Xaa (SEQ ID No. 15) Xaa-Trp-Yaa-Xaa SEQ ID No. 16) | broad specificity, max length = 40 amino acids |
| Renin followed by dipeptidyl-peptidase IV | Asp-Arg-Tyr-Ile-Pro-Phe-His-Leu-Val-Tyr-Ser (SEQ ID No. 17) | substitute Pro or Ala for Val & Ser |

*The N-terminal side of bolded amino acids is the specific target for the protease cleavage.

The invention, by several mechanisms, suppresses the degradation of the active ingredient linked to an MT by protease that would otherwise tend to cleave one or more of the peptide bonds of the active ingredient. The molecular structure of the active ingredient may further include other substituents or modifications. For example, salmon calcitonin, a preferred peptide active agent herein, can be amidated at its C-terminus. Both synthetic and natural peptides can be orally delivered in accordance with the invention.

Peptide active compounds of the invention include, but are not limited to, insulin, vasopressin, calcitonin (including not only the preferred salmon calcitonin, but other calcitonins as well). Other examples include calcitonin gene-related peptide, parathyroid hormone, luteinizing hormone-releasing factor, erythropoietin, tissue plasminogen activators, human growth hormone, adrenocorticototropin, various interleukins, enkephalin, glucagon-like peptide 1, and all analogs thereof. Many others are known in the art. It is expected that any pharmaceutical compound having peptide bonds which would be subject to cleavage in the gastrointestinal tract would benefit from oral delivery in accordance with the present invention because of the enhancement of absorption of such compounds from the intestine coupled with the reduction in such cleavage that is afforded by the present invention.

When salmon calcitonin is used, it preferably comprises from 0.02 to 0.2 percent by weight relative to the total weight of the overall pharmaceutical composition (exclusive of enteric coating) Salmon calcitonin is commercially available (for example, from BACHEM, Torrence, Calif.). Alternatively it may be synthesized by known methods, some of which are discussed briefly below. Other peptide active agents should be present at higher or lower concentrations depending on desired target blood concentrations for the active compound and its bioavailability in the oral delivery system of the invention.

Salmon calcitonin precursors may be made by either chemical or recombinant syntheses known in the art. Precursors of other amidated peptide active agents may be made in like manner. Recombinant production is believed to be significantly more cost effective. Precursors are converted to active salmon calcitonin by amidation reactions that are also known in the art. For example, enzymatic amidation is described in U.S. Pat. No. 4,708,934 and European Patent Publications 0 308 067 and 0 382 403. Recombinant production is preferred for both the precursor and the enzyme that catalyzes the conversion of the precursor to salmon calcitonin. Such recombinant production is discussed in *Biotechnology*, Vol. 11 (1993) pp. 64–70, which further describes a conversion of a precursor to an amidated product. The recombinant product reported there is identical to natural salmon calcitonin, and to salmon calcitonin produced using solution and solid phase chemical peptide synthesis.

The linking of an MT to an active peptide ingredient may also be made by either chemical or recombinant syntheses known in the art. By "linking" as used herein is meant that the biologically active peptide is associated with the MT in such a manner that when the MT crosses the cell membrane, the active peptide is also imported across the cell membrane. Examples of such means of linking include (A) linking the MT to the active peptide by a peptide bond, i.e., the two peptides (the peptide part of the MT and the active peptide) can be synthesized contiguously; (B) linking the MT to the active peptide by a non-peptide covalent bond (such as conjugating a signal peptide to a protein with a crosslinking reagent); (C) chemical ligation methods can be employed to create a covalent bond between the carboxy-terminal amino acid of an MT such as a signal peptide and the active peptide.

Examples of method (A) are shown below wherein a peptide is synthesized, by standard means known in the art, (Merrifield, J. Am. Chem. Soc. 85:2149–2154, 1963; and Lin et al., Biochemistry 27:5640–5645, 1988) and contains, in linear order from the amino-terminal end, a signal peptide sequence (the MT), an amino acid sequence that can be cleaved by a plasma protease, and a biologically active amino acid sequence. Such a peptide could also be produced through recombinant DNA techniques, expressed from a recombinant construct encoding the above-described amino acids to create the peptide. (Sambrook et al., Molecular Cloning: A Laboratory Manual, 2nd Ed., Cold Spring Harbor Laboratory, Cold Spring Harbor, N.Y., 1989).

For method (B), either a peptide bond, as above, can be utilized or a non-peptide covalent bond can be used to link the MT with the biologically active peptide, polypeptide or protein. This non-peptide covalent bond can be formed by methods standard in the art, such as by conjugating the MT to the peptide, polypeptide or protein via a crosslinking reagent, for example, glutaraldehyde. Such methods are standard in the art. (Walter et al., Proc. Natl. Acad. Sci. USA 77:5197; 1980).

For method (C), standard chemical ligation methods, such as using chemical crosslinkers interacting with the carboxy-terminal amino acid of a signal peptide, can be utilized. Such methods are standard in the art (Goodfriend et al., Science 143:1344; 1964, which uses water-soluble carbodiimide as a ligating reagent) and can readily be performed to link the carboxy terminal end of the signal peptide to any selected biologically active molecule.

The production of the preferred recombinant salmon calcitonin (rsCT) may proceed, for example, by producing glycine-extended salmon calcitonin precursor in *E. coli* as a soluble fusion protein with glutathione-S-transferase. The glycine-extended precursor has a molecular structure that is identical to active salmon calcitonin except at the C-terminal (where salmon calcitonin terminates-pro-$NH_2$, while the precursor terminates-pro-gly. An $\alpha$-amidating enzyme described in the publications above catalyzes conversion of precursors to salmon calcitonin. That enzyme is preferably recombinantly produced, for example, in Chinese Hamster Ovary (CHO) cells) as described in the Biotechnology article cited above. Other precursors to other amidated peptides may be produced in like manner. Peptides that do not require amidation or other additional functionalities may also be produced in like manner. Other peptide active agents are commercially available or may be produced by techniques known in the art.

The pH-Lowering Agent and Protease Inhibitor

The total amount of the pH-lowering compound to be administered with each administration of salmon calcitonin should preferably be an amount which, when it is released into the intestine, is sufficient to lower the local intestinal pH substantially below the pH optima for proteases found there. The quantity required will necessarily vary with several factors including the type of pH-lowering agent used (discussed below) and the equivalents of protons provided by a given pH-lowering agent. In practice, the amount required to provide good bioavailability is an amount which, when added to a solution of 10 milliliters of 0.1 M sodium bicarbonate, lowers the pH of that sodium bicarbonate solution to no higher than 5.5, and preferably no higher than 4.7, most preferably no higher than 3.5. Enough acid to lower pH, in the foregoing test, to about 2.8 may been used in some embodiments. Preferably at least 300 milligrams, and more preferably at least 400 milligrams of the pH-lowering agent are used in the pharmaceutical composition of the invention. The foregoing preferences relate to the total combined weight of all pH-lowering agents where two or more of such agents are used in combination. The oral formulation should not include an amount of any base which, when released together with the pH-lowering compound, would prevent the pH of the above-described sodium bicarbonate test from dropping to 5.5 or below.

The pH-lowering agent of the invention may be any pharmaceutically acceptable compound that is not toxic in the gastrointestinal tract and is capable of either delivering hydrogen ions (a traditional acid) or of inducing higher hydrogen ion content from the local environment. It may also be any combination of such compounds. It is preferred that at least one pH-lowering agent used in the invention have a pKa no higher than 4.2, and preferably no higher than 3.0. It is also preferred that the pH lowering agent have a solubility in water of at least 30 grams per 100 milliliters of water at room temperature.

Examples of compounds that induce higher hydrogen ion content include aluminum chloride and zinc chloride. Pharmaceutically acceptable traditional acids include, but are not limited to acid salts of amino acids (e.g. amino acid hydrochlorides) or derivatives thereof. Examples of these are acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine and valine.

Other examples of useful pH-lowering compounds include carboxylic acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, valeric, and the like.

Other useful pH-lowering agents that might not usually be called "acids" in the art, but which may nonetheless be useful in accordance with the invention are phosphate esters (e.g., fructose 1, 6 diphosphate, glucose 1, 6 diphosphate, phosphoglyceric acid, and diphosphoglyceric acid). CARBOPOL® (Trademark BF Goodrich) and polymers such as polycarbophil may also be used to lower pH.

Any combination of pH lowering agent that achieves the required pH level of no higher than 5.5 in the sodium bicarbonate test discussed above may be used. One preferred embodiment utilizes, as at least one of the pH-lowering agents of the pharmaceutical composition, an acid selected from the group consisting of citric acid, tartaric acid and an acid salt of an amino acid.

When salmon calcitonin is the peptide active agent, certain ratios of pH-lowering agent to salmon calcitonin have proven especially effective. It is preferred that the weight ratio of pH-lowering agent to salmon calcitonin exceed 200:1, preferably 800:1 and most preferably 2000:1.

An alternative or a supplement to the use of pH-lowering agents is the use of protease inhibitors, in particular inhibitors of intestinal proteases. The following Table 3 illustrates some of the known intestinal proteases.

TABLE 3

Intestinal Proteases and their Specific Targets

| PROTEASE | TARGET SITE | pH OPTIMUM | REMARKS |
|---|---|---|---|
| Trypsin | Lys-Xaa | 8 | |
| | Arg-Xaa | | |
| Chymotrypsin | Tyr-Xaa | 7.0–9.0 | |
| | Phe-Xaa | | |
| | Trp-Xaa | | |
| Elastase | Ala-Xaa | 8.8 | |
| | Val-Xaa | | |
| | Leu-Xaa | | |
| | Ile-Xaa | | |
| | Gly-Xaa | | |
| | Ser-Xaa | | |
| Kallikrein | Arg-Xaa | 7.0–8.0 | |
| | Phe-Arg-Xaa | | preferred |
| | Leu-Arg-Xaa | | preferred |
| Carboxypeptidase | Xaa-Xaa | 7.0–9.0 | from C-terminal |

Optional Ingredients—The Absorption Enhancer

When used, the absorption enhancers are preferably present in a quantity that constitutes from 0.1 to 20.0 percent by weight, relative to the overall weight of the pharmaceutical composition (exclusive of the enteric coating). Preferred absorption enhancers are surface active agents which act both as solubility enhancers and uptake enhancers. Generically speaking, "solubility enhancers" improve the ability of the components of the invention to be solubilized in either the aqueous environment into which they are originally released or into the lipophilic environment of the mucous layer lining the intestinal walls, or both. "Transport (uptake) enhancers" (which are frequently the same surface active agents used as solubility enhancers) are those which facilitate the ease by which peptide agents cross the intestinal wall.

One or more absorption enhancers may perform one function only (e.g., solubility), or one or more absorption enhancers may perform the other function only (e.g., uptake), within the scope of the invention. It is also possible to have a mixture of several compounds some of which provide improved solubility, some of which provide improved uptake and/or some of which perform both. Without intending to be bound by theory, it is believed that uptake enhancers may act by (1) increasing disorder of the hydrophobic region of the membrane exterior of intestinal cells, allowing for increased transcellular transport; or (2) leaching membrane proteins resulting in increased transcellular transport; or (3) widening pore radius between cells for increased paracellular transport.

Surface active agents are believed to be useful both as solubility enhancers and as uptake enhancers. For example, detergents are useful in (1) solubilizing all of the active components quickly into the aqueous environment where they are originally released, (2) enhancing lipophilicity of the components of the invention, especially the peptide active agent, aiding its passage into and through the intestinal mucus, (3) enhancing the ability of the normally polar peptide active agent to cross the epithelial barrier of the brush border membrane; and (4) increasing transcellular or paracellular transport as described above.

When surface active agents are used as the absorption enhancers, it is preferred that they be free flowing powders for facilitating the mixing and loading of capsules during the manufacturing process. Because of inherent characteristics of salmon calcitonin and other peptides (e.g., their isoelectric point, molecular weight, amino acid composition, etc.) certain surface active agents interact best with certain peptides. Indeed, some can undesirably interact with the charged portions of salmon calcitonin and prevent its absorption, thus undesirably resulting in decreased bioavailability. It is preferred, when trying to increase the bioavailability of salmon calcitonin or other peptides that any surface active agent used as an absorption enhancer be selected from the group consisting of (i) anionic surface active agents that are cholesterol derivatives (e.g., bile acids), (ii) cationic surface agents (e.g., acyl carnitines, phospholipids and the like), (iii) non-ionic surface active agents, and (iv) mixtures of anionic surface active agents (especially those having linear hydrocarbon regions) together with negative charge neutralizers. Negative charge neutralizers include but are not limited to acyl carnitines, cetyl pyridinium chloride, and the like. It is also preferred that the absorption enhancer be soluble at acid pH, particularly in the 3.0 to 5.0 range.

One especially preferred combination that has worked well with salmon calcitonin mixes cationic surface active agents with anionic surface active agents that are cholesterol derivatives, both of which are soluble at acid pH.

A particularly preferred combination is an acid soluble bile acid together with a cationic surface active agent. An acyl carnitine and sucrose ester is a good combination. When a particular absorption enhancer is used alone, it is preferred that it be a cationic surface active agent. Acyl carnitines(e.g., lauroyl carnitine), phospholipids and bile acids are particularly good absorption enhancers, especially acyl carnitine. Anionic surfactants that are cholesterol derivatives are also used in some embodiments. It is the intent of these preferences to avoid interactions with the peptide agent that interfere with absorption of peptide agent into the blood.

To reduce the likelihood of side effects, preferred detergents, when used as the absorption enhancers of the invention, are either biodegradable or reabsorbable (e.g. biologically recyclable compounds such as bile acids, phospholipids, and/or acyl carnitines), preferably biodegradable. Acylcarnitines are believed particularly useful in enhancing paracellular transport. When a bile acid (or another anionic detergent lacking linear hydrocarbons) is used in combination with a cationic detergent, salmon calcitonin is better transported both to and through the intestinal wall.

Preferred absorption enhancers include: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.); (d) anionic surfactants such as dioctyl sodium sulfosuccinate; (e) lyso-phospholipids such as lysolecithin and lysophosphatidylethanolamine; (f) acylcarnitines, acylcholines and acyl amino acids such as lauroylcarnitine, myristoylcarnitine, palmitoylcarnitine, lauroylcholine, myristoylcholine, palmitoylcholine, hexadecyllysine, N-acylphenylalanine, N-acylglycine etc.; g) water soluble phospholipids; (h) medium-chain glycerides which are mixtures of mono-, di- and triglycerides containing medium-chain-length fatty acids (caprylic, capric and lauric acids); (i) ethylene-diaminetetraacetic acid; (j) cationic surfactants such as cetylpyridinium chloride; (k) fatty acid derivatives of polyethylene glycol such as Labrasol, Labrafac, etc.; and (1) alkylsaccharides such as lauryl maltoside, lauroyl sucrose, myristoyl sucrose, palmitoyl sucrose, etc.

In some preferred embodiments, and without intending to be bound by theory, cationic ion exchange agents (e.g. detergents) are included to provide solubility enhancement by another possible mechanism. In particular, they may prevent the binding of salmon calcitonin or other peptide active agents to mucus. Preferred cationic ion exchange agents include protamine chloride or any other polycation.

Other Optional Ingredients

It is preferred that a water-soluble barrier separate the protease inhibitors and/or the pH-lowering agent from the acid resistant protective vehicle. A conventional pharmaceutical capsule can be used for the purpose of providing this barrier. Many water soluble barriers are known in the art and include, but are not limited to, hydroxypropyl methylcellulose and conventional pharmaceutical gelatins.

In some preferred embodiments, another peptide (such as albumin, casein, soy protein, other animal or vegetable proteins and the like) is included to reduce non-specific adsorption (e.g., binding of peptide to the intestinal mucus barrier) thereby lowering the necessary concentration of the expensive peptide active agent. When added, the peptide is preferably from 1.0 to 10.0 percent by weight relative to the weight of the overall pharmaceutical composition (excluding protective vehicle). Preferably, this second peptide is not physiologically active and is most preferably a food peptide such as soy bean peptide or the like. Without intending to be bound by theory, this second peptide may also increase bioavailability by acting as a protease scavenger that desirably competes with the peptide active agent for protease interaction. The second peptide may also aid the active compound's passage through the liver.

All pharmaceutical compositions of the invention may optionally also include common pharmaceutical diluents, glidents, lubricants, gelatin capsules, preservatives, colorants and the like in their usual known sizes and amounts.

The Protective Vehicle

Any carrier or vehicle that protects the salmon calcitonin from stomach proteases and then dissolves so that the other ingredients of the invention may be released in the intestine is suitable. Many such enteric coatings are known in the art, and are useful in accordance with the invention. Examples include cellulose acetate phthalate, hydroxypropyl methylethylcellulose succinate, hydroxypropyl methylcellulose phthalate, carboxyl methylethylcellulose and methacrylic acid-methyl methacrylate copolymer. In some embodiments, the active peptide, absorption enhancers such as solubility and/or uptake enhancer(s), and pH-lowering compound(s), are included in a sufficiently viscous protective syrup to permit protected passage of the components of the invention through the stomach.

Suitable enteric coatings for protecting the peptide agent from stomach proteases may be applied, for example, to capsules after the remaining components of the invention have been loaded within the capsule. In other embodiments, enteric coating is coated on the outside of a tablet or coated on the outer surface of particles of active components which are then pressed into tablet form, or loaded into a capsule, which is itself preferably coated with an enteric coating.

It is very desirable that all components of the invention be released from the carrier or vehicle, and solubilized in the intestinal environment as simultaneously as possible. It is preferred that the vehicle or carrier release the active components in the small intestine where uptake enhancers that increase transcellular or paracellular transport are less likely to cause undesirable side effects than if the same uptake enhancers were later released in the colon. It is emphasized, however, that the present invention is believed effective in the colon as well as in the small intestine. Numerous vehicles or carriers, in addition to the ones discussed above, are known in the art. It is desirable (especially in optimizing how simultaneously the components of the invention are released) to keep the amount of enteric coating low. Preferably, the enteric coating adds no more than 30% to the weight of the remainder of pharmaceutical composition (the "remainder" being the pharmaceutical composition exclusive of enteric coating itself). More preferably, it adds less than 20%, especially from 12% to 20% to the weight of the uncoated composition. The enteric coating preferably should be sufficient to prevent breakdown of the pharmaceutical composition of the invention in 0.1N HCl for at least two hours, then capable of permitting complete release of all contents of the pharmaceutical composition within thirty minutes after pH is increased to 6.3 in a dissolution bath in which said composition is rotating at 100 revolutions per minute.

Other Preferences

It is preferred that the weight ratio of pH-lowering agent (s)and/or protease inhibitors to absorption enhancer(s), when present, be between 3:1 and 20:1, preferably 4:1–12:1, and most preferably 5:1–10:1. The total weight of all pH-lowering agents and/or protease inhibitors and the total weight of all absorption enhancers in a given pharmaceutical composition is included in the foregoing preferred ratios. For example, if a pharmaceutical composition includes two pH-lowering agents and three absorption enhancers, the foregoing ratios will be computed on the total combined weight of both pH-lowering agents and the total combined weight of all three absorption enhancers.

It is preferred that the pH-lowering agent and/or protease inhibitor, the peptide active agent and the absorption enhancer, when present, (whether single compounds or a plurality of compounds in each category) be uniformly dispersed in the pharmaceutical composition. In one embodiment, the pharmaceutical composition comprises granules that include a pharmaceutical binder having the peptide active agent, the pH-lowering agent and the absorption enhancer uniformly dispersed within said binder. Preferred granules may also consist of an acid core, surrounded by a uniform layer of organic acid, a layer of enhancer and a layer of peptide that is surrounded by an outer layer of organic acid. Granules may be prepared from an aqueous mixture consisting of pharmaceutical binders such as polyvinyl pyrrolidone or hydroxypropyl methylcellulose, together with the pH-lowering agents, absorption enhancers and peptide active agents of the invention.

Manufacturing Process

A preferred pharmaceutical composition of the invention includes a size OO gelatin capsule filled with 0.25 mg. of salmon calcitonin linked to an MT, 400 mg. of granular citric acid (available for example from Archer Daniels Midland Corp.), 50 mg. of taurodeoxycholic acid (available for example from SIGMA), 50 mg. lauroyl carnitine (SIGMA).

All of the ingredients are preferably for eventual insertion into the gelatin capsule, and are preferably powders which may be added to a blender in any order. Thereafter, the blender is run for about three minutes until the powders are thoroughly intermixed. Then the mixed powders are loaded into the large end of the gelatine capsules. The other end of the capsule is then added, and the capsule snapped shut. 500 or more such capsules may be added to a coating device (e.g., Vector LDCS 20/30 Laboratory Development Coating System (available from Vector Corp., Marion, Iowa)).

An enteric coating solution is made as follows. Weigh 500 grams of EUDRAGIT L30 D-55 (a methacrylic acid copolymer with methacylic acid methyl ester, an enteric coating available from RoHM Tech Inc., Maidan, Mass.). Add 411 grams distilled water, 15 grams triethyl citrate and 38 grams talc. This amount of coating will be sufficient to coat about 500 size OO capsules.

The capsules are weighed and placed into the drum of the coating machine. The machine is turned on to rotate the drum (now containing capsules) at 24–28 rpm. The temperature of inlet sprayer is preferably about 45° C. Exhaust temperatures are preferably about 30° C. Uncoated capsule temperature is preferably about 25° C. Air flow is about 38 cubic feet per minute.

A tube from the machine is then inserted into the coating solution prepared as discussed above. The pump is then turned on for feeding solution into the coating device. Coating then proceeds automatically. The machine can be stopped at any time to weigh capsules to determine if the coating amount is sufficient. Usually coating is allowed to proceed for 60 minutes. The pump is then turned off for about five minutes while the machine is still running to help dry the coated capsules. The machine can then be turned off. The capsule coating is then complete, although it is recommended that the capsules be air dried for about two days.

Because of the enhanced bioavailability provided by the present invention, the concentration of expensive salmon calcitonin in the pharmaceutical preparation of the invention may be kept relatively low. Specific formulation examples are set forth in examples infra.

Treatment of Patients

When salmon calcitonin is chosen as active ingredient for treatment of osteoporosis, periodic administration is recommended. Salmon calcitonin is metabolized quickly with a half-life of only 20–40 minutes following subcutaneous administration in man. However, its beneficial effect on osteoclasts is much longer lasting, and may last for more than 24 hours notwithstanding rapid decrease in blood levels. There is usually no detectable blood levels more than two hours after injection of salmon calcitonin at conventional dosages. Accordingly, periodic administration of one dose about 5 days per week is preferred. Subcutaneous administration of salmon calcitonin (100 International units) has frequently resulted in peak serum concentration of about 250 picograms per milliliter. Nasally administered salmon calcitonin (200 International units) has proven effective against osteoporosis at peak levels as low as 10 picograms per milliliter. Some patients report some gastrointestinal distress at high peak levels (e.g. at or above 200 picograms per milliliter). Accordingly, it is preferred that serum salmon calcitonin peak between 10 and 150 picograms per milliliter, more preferably between 10 and 50 picograms per milliliter. The serum levels may be measured by radioimmunoassay techniques known in the art. The attending physician may monitor patient response, salmon calcitonin blood levels, or surrogate markers of bone disease (such as urinary pyridinoline or deoxypyridinoline), especially during the initial phase of treatment (1–6 months). He may then alter the dosage somewhat to account for individual patient metabolism and response.

The bioavailability achievable in accordance with the present invention permits oral delivery of salmon calcitonin into the blood at the above-identified preferred concentration levels while using only 10–1000 micrograms of salmon calcitonin per capsule, preferably 10–400 micrograms, especially between 10 and 200 micrograms.

It is preferred that a single capsule be used at each administration because a single capsule best provides simultaneous release of the polypeptide, pH-lowering agent and absorption enhancers. This is highly desirable because the acid is best able to reduce undesirable proteolytic attack on the polypeptide when the acid is released in close time proximity to release of the polypeptide. Near simultaneous release is best achieved by administering all components of the invention as a single pill or capsule. However, the invention also includes, for example, dividing the required amount of acid and enhancers, when used, among two or more capsules which may be administered together such that they together provide the necessary amount of all ingredients. "Pharmaceutical composition," as used herein includes a complete dosage appropriate to a particular administration to a human patient regardless of how it is subdivided so long as it is for substantially simultaneous administration.

EXAMPLE 1

Preparation of A Purified Fusion Peptide of Salmon Calcitonin (sCT) and Enzyme-Cleavable Membrane Translocator (MT)

1. Construction of Fusion Peptide of Salmon Calcitonin (sCT) and Enzyme-Cleavable Membrane Translocator (MT)

A membrane translocator sequence corresponding to the Protein Transduction Domain of the HIV TAT protein was used. The amino acid sequence of this MT is as follows:
TYR-GLY-ARG-LYS-LYS-ARG-ARG-GLN-ARG-ARG-ARG (SEQ ID NO: 18).

Downstream of this MT sequence is the enzyme cleavable sequence TRP-VAL-ALA. This is followed by the 33 amino acid sequence for sCT-Gly:

(SEQ ID No.19)
CYS-SER-ASN-LEU-SER-THR-CYS-VAL-LEU-GLY-LYS-LEU-

-continued

SER-GLN-GLU-LEU-HIS-LYS-LEU-GLN-THR-TYR-PRO-ARG-
THR-ASN-THR-GLY-SER-GLY-THR-PRO-GLY

The resulting fusion sequence is shown schematically below:

| MEMRANE TRANSLOCATOR | TRP-VAL-ALA | SALMON CALCITONIN-GLY |
|---|---|---|

The TRP-VAL-ALA sequence is enzyme-cleavable first by endothelin converting enzyme between TRP and VAL and the resulting VAL-ALA-sCT-GLY sequence is cleavable by dipeptidyl-peptidase IV to liberate authentic sCT-Gly.

The DNA sequence for this fusion was assembled as follows:

Two synthetic oligonucleotides are made:

Oligo 1 (+) 57:    (SEQ ID No.20)
5'-CCTACGGTCGTAAAAAACGTCGTCAGCGTCGTCGTTGGGTTGCGTGT
TCTAACTTGT-3'

Oligo 2 (-) 59:    (SEQ ID No.21)
5'-AGACAAGTTAGAACACGCAACCCAACGACGACGCTGACGACGTTTTT
TACGACCGTAGG-3'

Oligos 1 and 2 encode the MT sequence plus an amino acid at the 5' end for ligation into the appropriate vector, the enzyme cleavable sequence, and the first 4 amino acids of the sCT-Gly sequence (CYS-SER-ASN-LEU) (SEQ ID NO:22). The minus strand oligonucleotide was phosphorylated at the 5' end. The double stranded DNA sequence was assembled by annealing and ligation of Oligo 1 and Oligo 2. The overhang formed at the 3' end gave an Acc I compatible sticky end.

Figure 3:
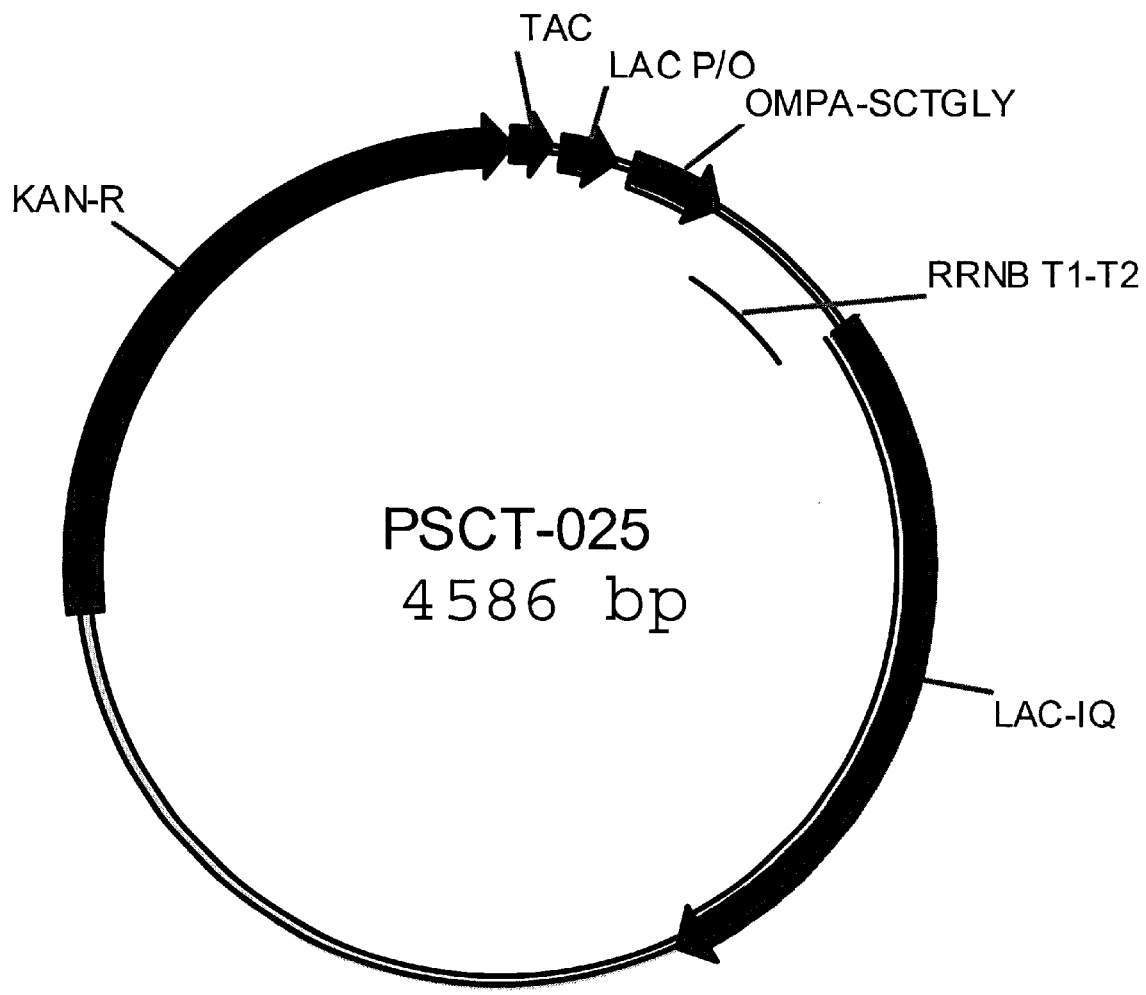
FIG. 3 shows the circular plasmid map of the pSCT025 vector containing the sCT gene.

The gene for sCT-Gly was obtained by PCR amplification of the appropriate region from plasmid, psCT025, which is a previously constructed expression plasmid containing the sCT gene (see FIG. 3), or from any other suitable source of the sCT gene. The primers used for the PCR amplification generated a 125 bp amplified fragment that contains the entire sCT gene. PCR amplification was done using a commercially available kit from Boehringer Mannheim. The PCR cycling was done as follows:

94° C.-2 min-1 cycle

94° C.-30 sec-45° C.-1 min-68° C.-1 min-5 cycles

94° C.-30 sec-65° C.-1 min-68° C.-1 min-25 cycles

68° C.-5 min-1 cycle

4° C.-soak.

The 5'-PCR primer contains an Acc I site, and the 3' primer contains a Nco I site. The 125 bp PCR fragment was digested with Acc I and the resulting 100 bp fragment was isolated from an agarose gel and quantified. The double stranded DNA fragment formed by ligation of oligos 1 and 2 was now ligated to the 100 bp PCR fragment at the common Acc I site. The product of this ligation was digested with Nco I. The resulting 150 bp DNA sequence had a blunt 5' end and a Nco I compatible 3' end. This DNA fragment, designated MT3sCT01, was gel purified and quantified.

2. Cloning of MT3sCT01 into the DUSEC-05 Universal Secretion Vector.

Figure 1:
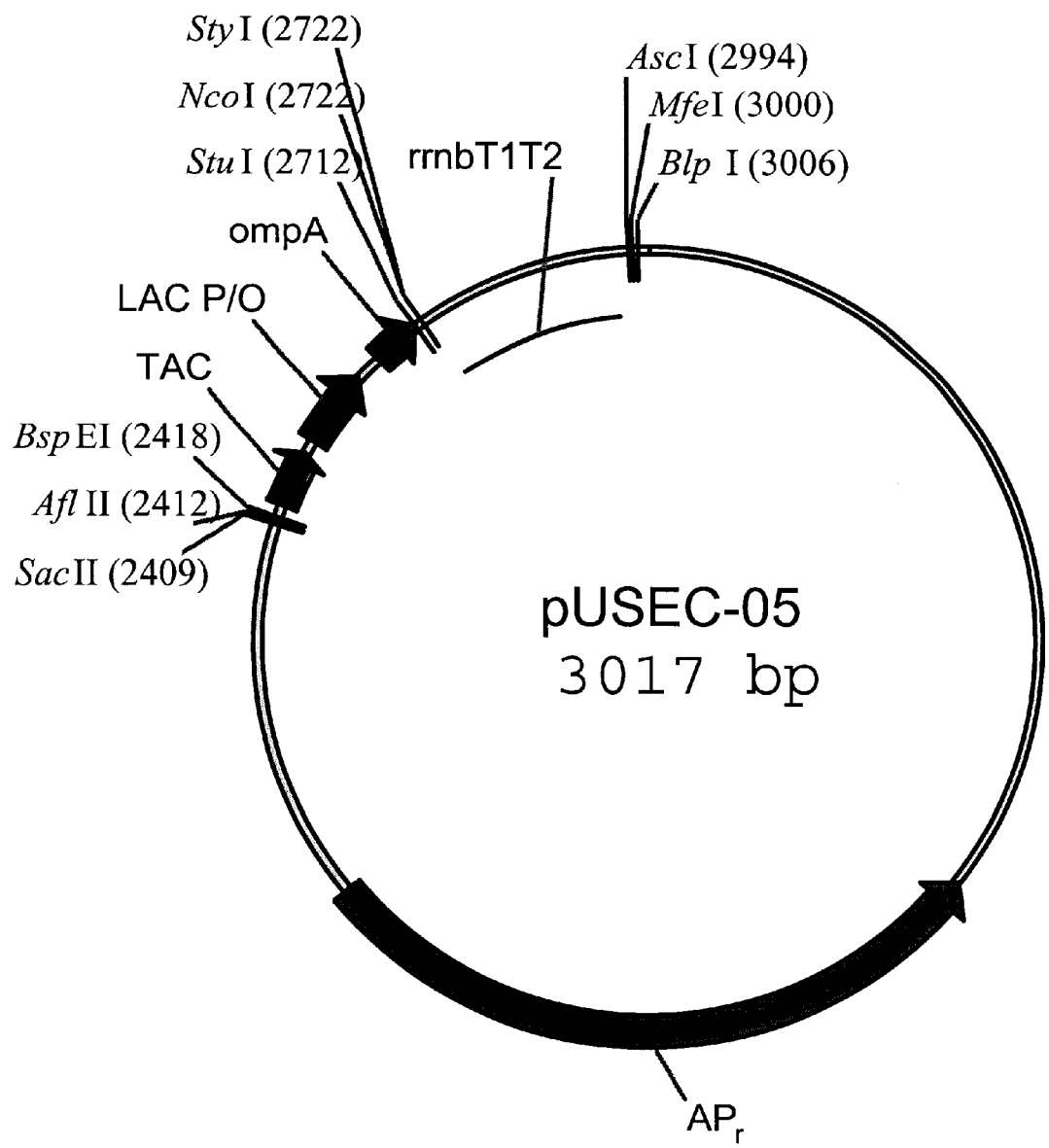
FIG. 1 shows the circular plasmid map of the Universal Cloning Vector pUSEC-05.
Figure 2:
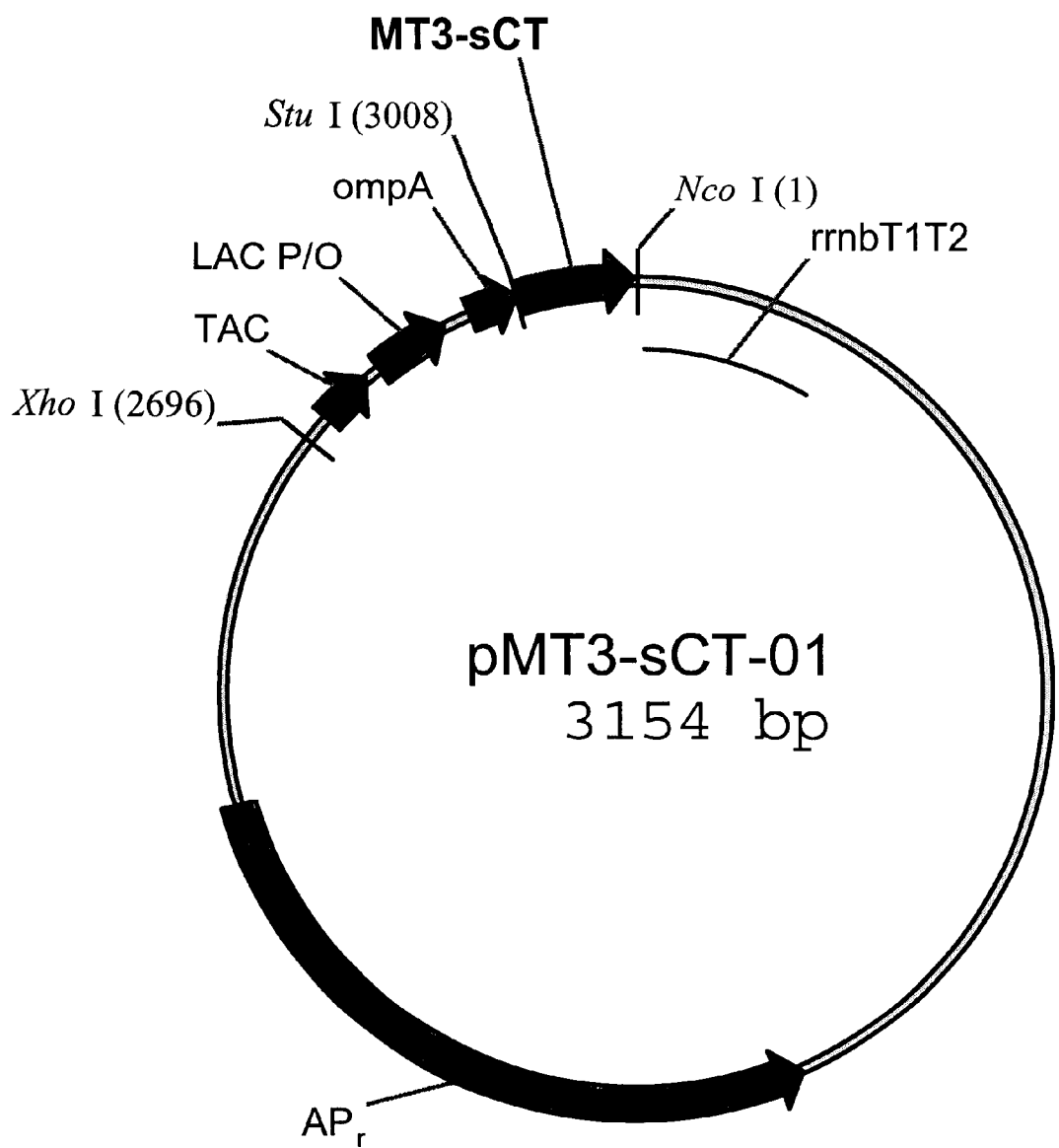
FIG. 2 shows the circular plasmid map of pMT3-sCT-01, a vector for the expression of the MT-sCT fusion sequence.

The universal cloning vector pUSEC-05 (FIG. 1), contains dual Tac and Lac promoters, followed by a Shine-Delgarno sequence and the sequence for the omp A signal peptide. Downstream of the omp A signal are cloning sites for Stu I, Nco I, and Sty I. pUSEC-05 was linearized by digestion with Stu I and Nco I and MT3sCT01 sequence was ligated into the vector at blunt ends on the 5' end and the Nco I site on the 3' end to create the plasmid pMT3sCT01 (FIG. 2). The MT3sCT01 plasmid was characterized by restriction digest mapping and sequencing to confirm the presence of all relevant genes and the sequence of the cloned DNA fragment.

This plasmid was used to transform the host strain E. coli BLR to create the recombinant expression strain UGL286.

3. Cloning of MT3sCT01 into the pUSEC-06 Universal Secretion Vector

Figure 4:
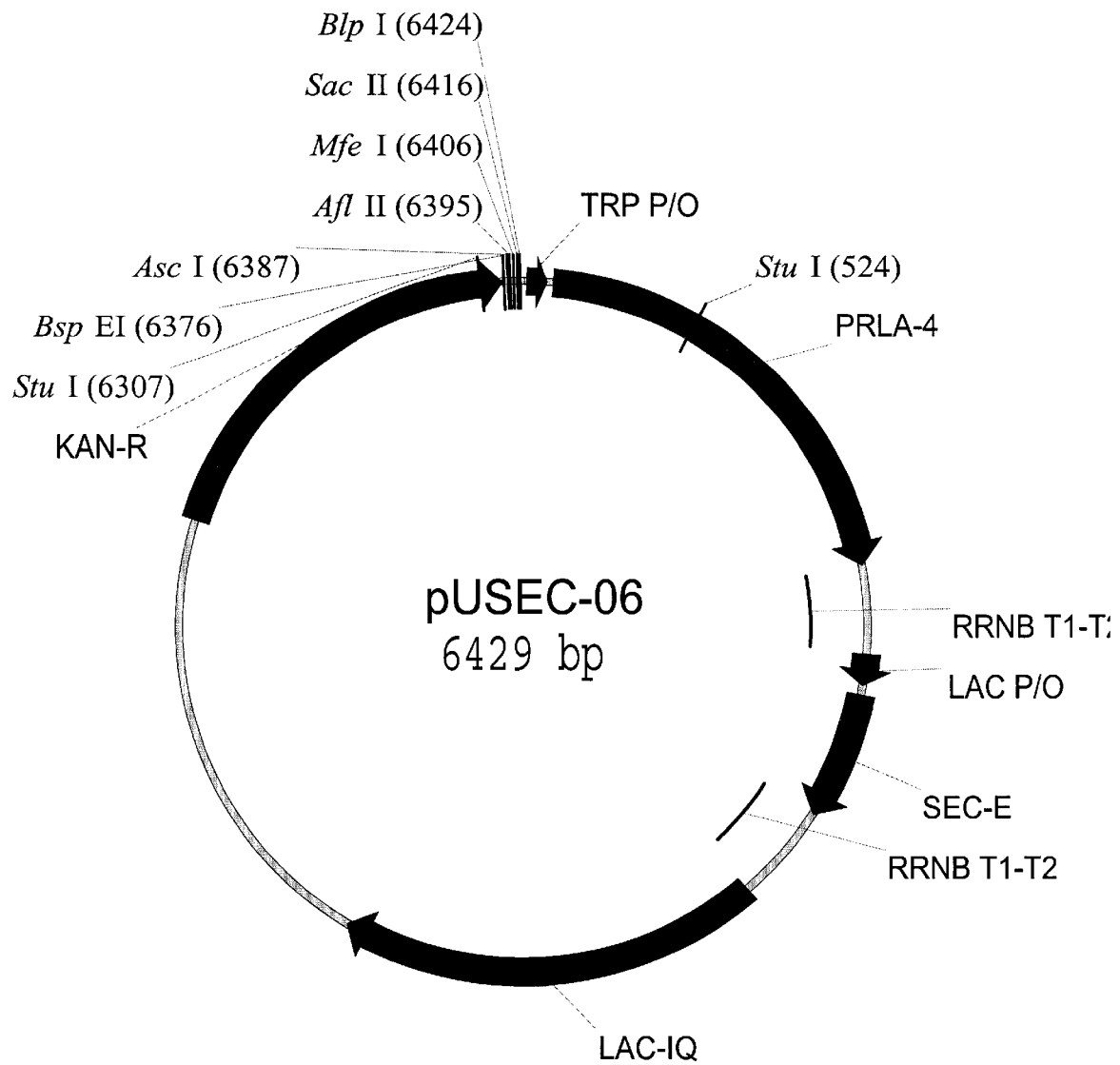
FIG. 4 shows the circular plasmid map of the Universal Cloning Vector pUSEC-06.
Figure 5:
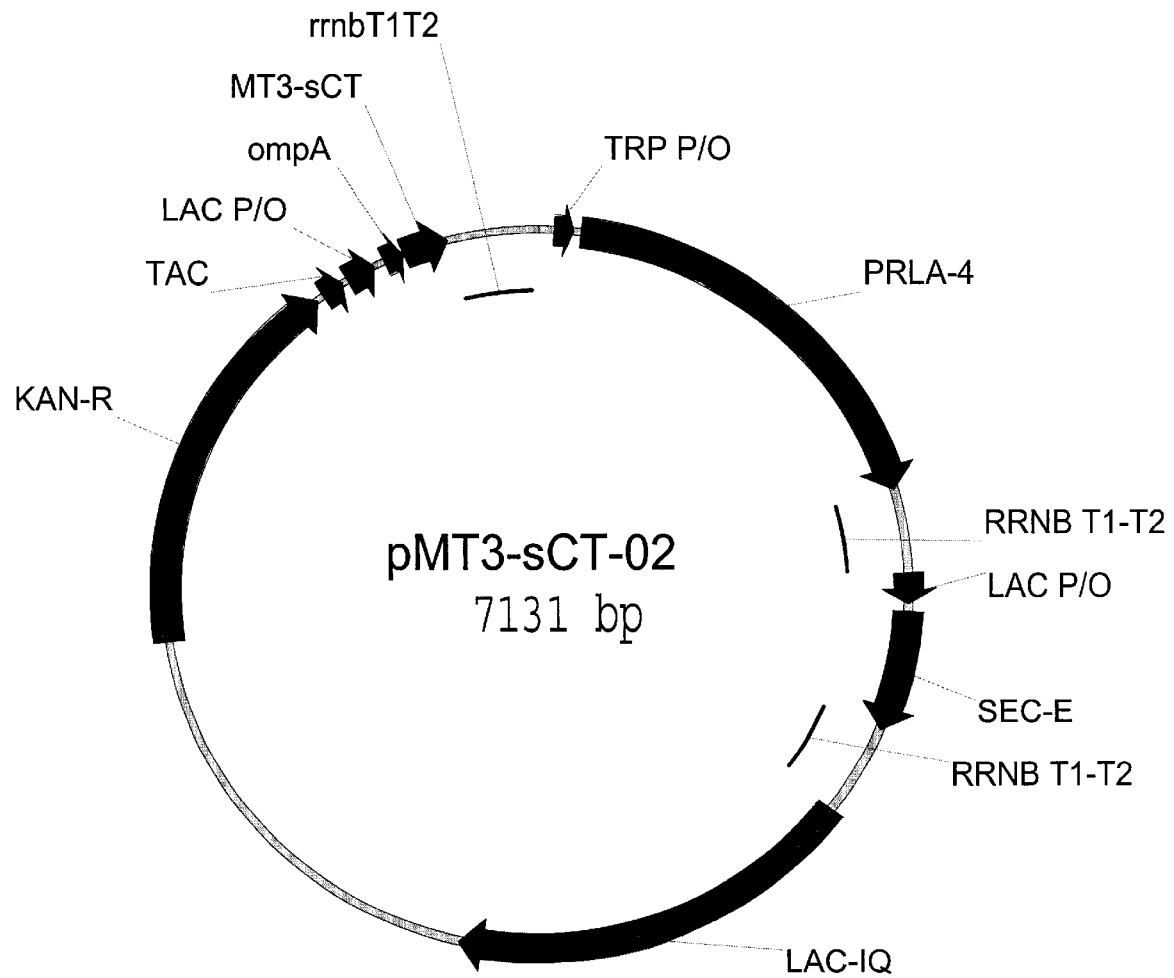
FIG. 5 shows the circular plasmid map of pMT3-sCT-02, a vector for the expression of the MT-sCT fusion sequence.

The universal cloning vector pUSEC-06 (FIG. 4), contains dual Tac and Lac promoters, followed by a Shine-Delgarno sequence and the sequence for the ompA signal peptide. The Multiple Cloning Site [MCS] of the pUSEC06 plasmid vector contains the restriction enzyme sites for BspE1 and Asc 1 The pUSEC-06 was linearized by digestion with these enzymes, creating sticky ends for directional ligation. The plasmid, pMT3sCT01, was cut with BspE1 and Asc 1 as well, and the 713 bp DNA fragment containing the MT3sCT01 DNA sequence was isolated, gel purified, and quantified. The MT3sCT01 sequence was directionally ligated into the vector with the BspE1 at the 5' end and the Asc1 site on the 3' end to create the plasmid, pMT3-sCT-02 (FIG. 5).

4. Cloning of MT3sCT as a Double Gene Cartridge

Figure 6:
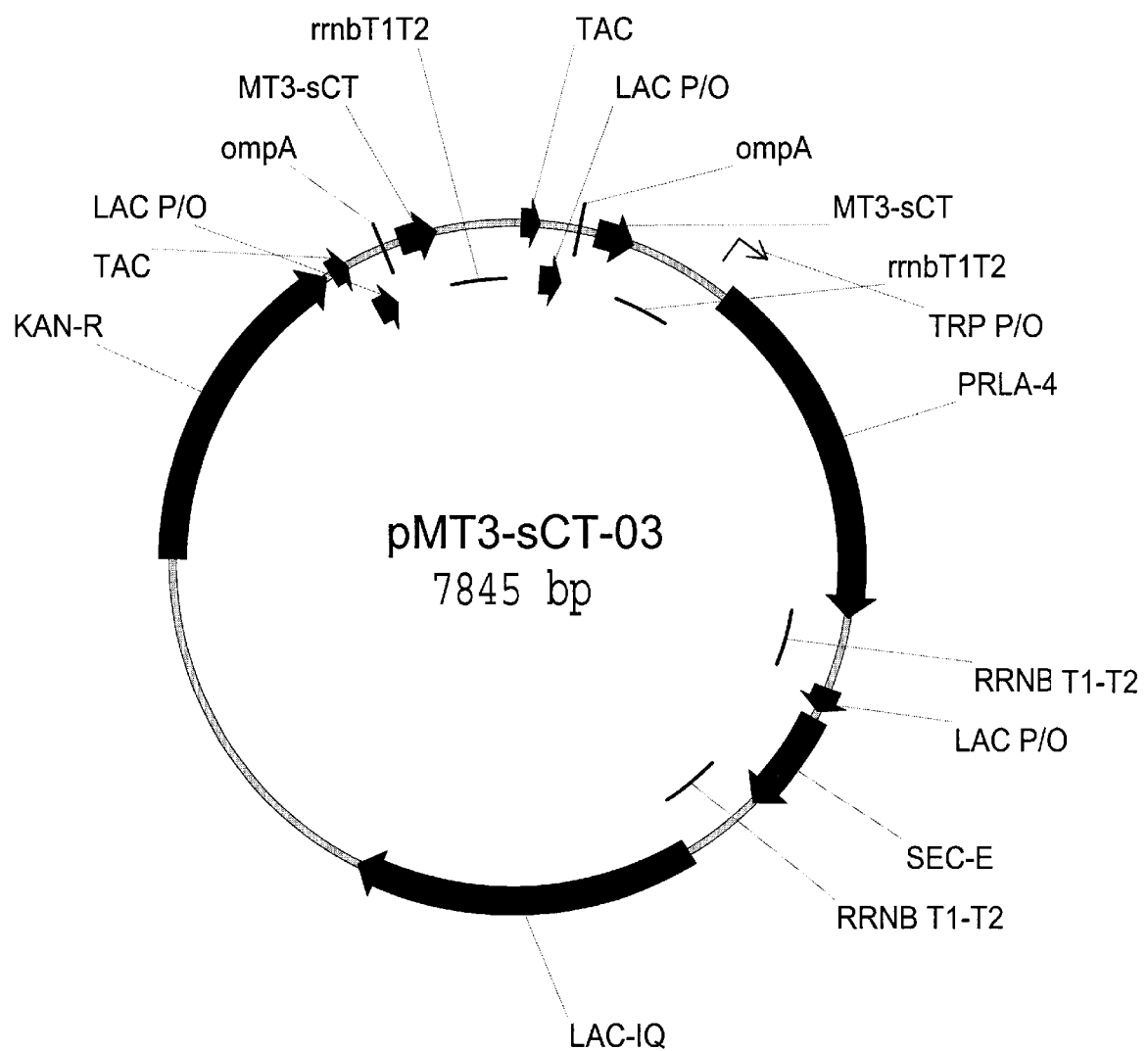
FIG. 6 shows the circular plasmid map of pMT3-sCT-03, a vector for the expression of the MT-sCT fusion sequence.

The pMT-sCT-02 plasmid was linearized with 2 other restriction enzymes, AflII and Mfe I, with sites within the MCS immediately adjacent to each other. The pMTsCT01 plasmid was also cut with the same two enzymes to release the DNA fragment MT3sCT01. The isolated, gel purified DNA fragment was directionally cloned into the vector at the Afl II/Mfe compatible ends to create the plasmid pMT3-sCT-03 (FIG. 6), which encodes tandem MT3sCT01 sequences, as well as the kanamycin resistance gene, the lacIQ gene, and the secretion factor genes, secE and prlA4.

The pMT3-sCT-03 plasmid was used to transform competent E. coli BLR cells to create the recombinant expression strain, UGL 716.

5. Fermentation, and Analysis

The expression strain, UGL 716, was grown in bench scale fermentation according to Series 700 Fermentation Protocol, ref. CPM:022:035, under standard conditions of pH, $dO_2$, temperature and feeding/induction regime. The fermentation was harvested by centrifugation at 26 hours and the cells were stored at −20 C. until lysis. The fermentation samples were evaluated by DNA analysis and protein expression analysis.

DNA analysis: Restriction enzyme mapping analysis of the plasmid prepared from the fermentation samples verified the presence of pMT3sCT03 plasmid and all relevant genes.

Protein expression analysis of the fermentation samples by SDS-PAGE [mini-Protean system w/10–20% gradient gels] and western blot/immunoassay confirmed the production of an insoluble protein that reacted positively with an sCT-specific polyclonal antibody.

6. Cell Lysis and Isolation of Insoluble Fraction

About 124 g [wcw] of harvested cells from the UGL 716 fermentation were lysed using the Rannie 8.30H homogenizer at ~12K psi in a Tris/NaCl lysis buffer, pH 8.5 plus $MgCl_2$ and ~32K units of Benzonase™. The resulting total lysate was centrifuged at 9K rpm for 1 hour. The sup was removed and the pellet was washed once with Tris/NaCl lysis buffer and re-centrifuged. The remaining insoluble pellet was used for solubilization and purification of the recombinant protein.

7. Solubilization and Purification

Approximately 54 grams (wet weight) of *E. coli* inclusion bodies were partially solublized with 800 mL 0.1 M HCl, 5 M guanidine HCl. The suspension was centrifuged at 20,000 rpm (50,000×g) for 60 minutes. The resultant supernatant was collected and loaded directly onto a Vydac C18 (22×250 mm), 10 m, 300 column equilibrated with 0.1% trifluoroacetic acid. The column was subjected to a linear gradient from 100% A (0.1% TFA) to 100% B (0.1% trifluoroacetic, 80% acetonitrile) over 90 minutes. The column was operated at 25 mL/min. and the UV absorbance was monitored at 280 nm. Collected fractions were screened and pooled following RP-HPLC analysis on a Vydac C18 (4.6×250 mm), 5 m, 300 column. The pooled fractions were concentrated to dryness by lyophilization to afford 133 mg of white powder. The purified peptide was subjected to amino acid composition analysis using pre-column derivatization with phenyl-isothiocyanate (PITC) and RP-HPLC analysis. The identity of the peptide was confirmed by electrospray mass spectroscopy (ESI-MS) analysis. The experimental average molecular mass was determined to be 7,416.92 Da, which was consistent with the expected molecular mass of the MT3sCTgly with the OmpA signal still attached to the molecule.

8. Analysis of Purified Recombinant OmpA-MT3-sCTgly by SDS-PAGE

Figure 7:
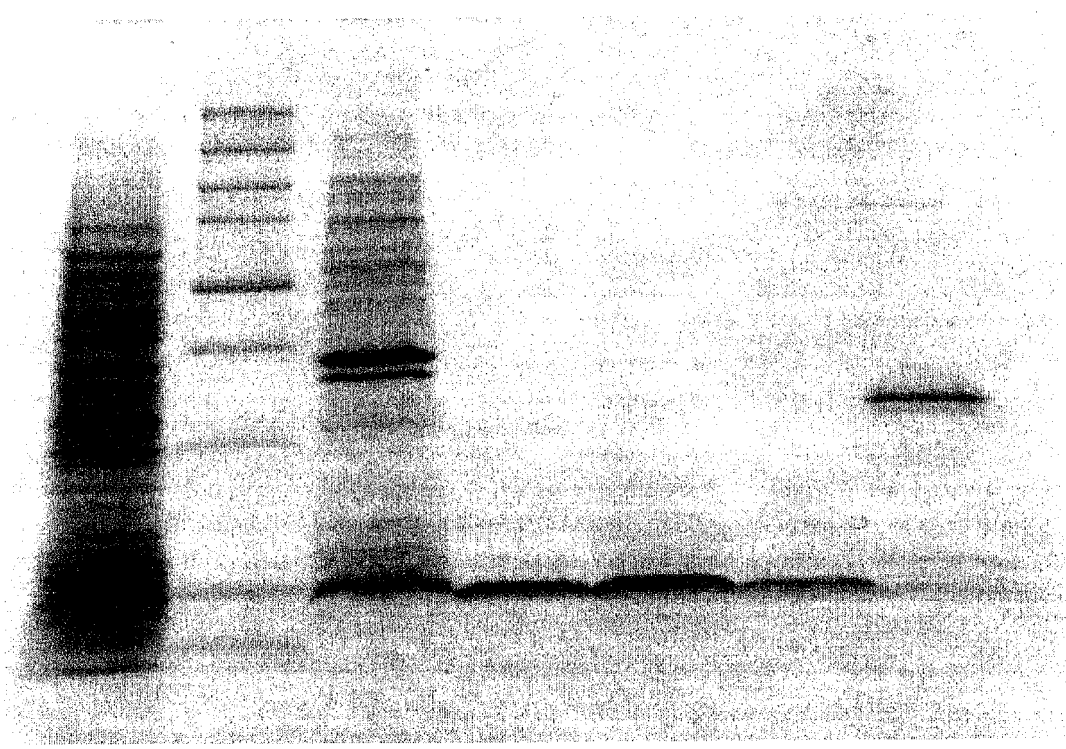
FIG. 7 shows a 10–20% gradient SDS-PAGE gel for the following samples.

A 10–20% gradient SDS-PAGE gel was used to analyze the samples listed in the Legend to FIG. 7. The gel analysis indicated that the insoluble material used as the input to the solubilization and purification contained the MTS3sCTgly protein [lane 3], migrating with the 15 kDa marker protein [lane 2]. The same band is seen in the different purification samples [lanes 4–6]. A positive control for the immunoblot GSTsCTgly, is seen in lane 7, while the negative control, a total lysate sample for a *E. coli* cell line, is seen in lane 1.

Using standard western blotting and immunoassay protocols an identical gel was transferred to PVDF membrane, the sCT-specific antibody was used at a 1:10,000 dilution and the color development was incubated for 1 minute (FIG. 8). The western blot above shows a low level of non-specific antibody reactivity in the negative control [lane 1]. Lane 2, the Precision Standards™ does not react with the antibody, although the marker proteins are designed to transfer to the membrane for easy reference. Lane 3 is the input, while lanes 4–6 are the analytical and preparative purification samples.

9. Conclusions from the Analyses

The putative MTS3sCTgly recombinant protein was in the insoluble fraction. The migration was not consistent with a predicted size of ~5 kDa for the MTS3sCTgly peptide, instead, the r-protein on the gel was migrating nearly coincident with the ~15 kDa marker protein. The fractionation and the gel analysis data also suggested that the signal peptide might be unprocessed in this construct, and this is corroborated by the data from amino acid analysis and mass spectroscopy. The total size of a protein composed of unprocessed OmpA/MTS3/sCTgly would be ~7 KDa. However, because of the highly charged nature of the MTS3, it is believed that the entire insoluble recombinant protein is running aberrantly, and giving rise to the 15 KDa size seen on the SDS-PAGE. Accordingly, the result of this process was the isolation of a fusion OmpA/MTS3/sCTgly protein, i.e. salmon calcitonin fused to two Mts, the OmpA signal peptide and MTS3.

EXAMPLE 2

Effect of OmPA-MT3 on the Absorption of Salmon Calcitonin from Rat Duodenum

Female Sprague-Dawley rats (250–275 g) (n=4 for each peptide) were anesthetized with ketamine and xylazine prior to the insertion of a cannula in the carotid artery. The cannula was fitted to a three way valve through which blood was sampled and replaced with physiological saline containing heparin. A midline incision was made in the abdominal cavity, and 0.45 mL of either sCT-gly (10 mg/mL) or OmpA-MT3-sCT-gly (10 mg/mL) in 0.5M citric acid was injected directly into the duodenum. Blood (0.5 ml) was collected before and at 5, 15, 30, 45 and 60 minutes after administration of the peptides. The blood was centrifuged, and the concentration (± SEM [standard error of the mean]) of sCT-gly or OmpA-MT3-sCT-gly in the plasma supernatant was determined by a competitive enzyme immunoassay (EIA). Peak plasma concentration (Cmax) was determined by inspection. The absolute bioavailbilty of each peptide (relative to an intravenous dose of sCT [salmon calcitonin]) was calculated from plots of the plasma concentration of each peptide as a function to time.

The results summarized in the Table 1 below show that the maximum concentration of each peptide in the blood occurred between 30 and 60 minutes after their administration. The Cmax of OmpA-MT3-sCT-gly was more than 25 fold greater than that of sCT-gly, and the bioavailability of OmpA-MT3-sCT-gly was more than 20 times greater than that of sCT-gly. These results clearly indicate that attaching OmpA-MT3 to sCTgly significantly enhances peptide absorption through the intestinal wall.

TABLE 1

Effect of OmpA-MT3 on the Absorption of sCT-gly from the Rat Duodenum

| Time min | sCT-gly ng/mL ± SEM | OmpA-MT3-sCT-gly ng/mL ± SEM |
|---|---|---|
| 0 | 0.00 | 0.00 |
| 5 | 200.62 ± 73.67 | 563.07 ± 150.44 |
| 15 | 115.53 ± 39.10 | 1861.86 ± 713.20 |
| 30 | 222.66 ± 44.76 | 5603.76 ± 1749.75 |
| 45 | 151.36 ± 107.43 | 3879.76 ± 713.62 |
| 60 | 178.60 ± 76.15 | 6060.70 ± 2462.69 |
| Cmax (ng/mL) | 222.66 ± 44.76 | 6060.70 ± 2462.69 |
| Absolute bioavailability (percent) | 0.92 ± 0.23 | 21.26 ± 6.23 |

EXAMPLE 3

Effect of the HIV TAT Protein Transduction Domain as an MT on the Absorption of Salmon Calcitonin from Dog Duodenum 1. Encapsulation and Oral Delivery OF MT3sCT01 Fusion Peptide in Dogs Two formulations are used to test the efficacy of MT3-sCT-01 fusion peptide.

The first formulation (F1) is prepared by blending 13 g citric acid, 1.3 g lauroylcarnitine, 0.65 g talc and 0.03 g sCT with a mortar and pestle. The other formulation (F2) is prepared by blending the same mixture except that sCT is replaced with an equivalent amount of MT3sCT01. Both blends are used to fill size 00 gelatin capsules, and the capsules are coated with Eudragit L30D-55. The resulting enteric-coated capsules contain approximately 1 to 2 mg of either sCT (F1) or MT3sCT01 (F2) per capsule. Fasted dogs (n=8) are administered F1 by mouth and blood samples are collected in heparinized tubes at t=−10 min, 0 min, and every 15 min thereafter for 240 minutes. The blood samples are centrifuged, and the resulting plasma stored at −20° C. for further analysis. After a 1 week washout period, the same dogs are given F2 by mouth, and the same protocol is followed.

2. Determination of Bioavailability of Salmon Calcitonin in Dog Plasma

The amount of sCT in plasma samples of dogs given either of the two formulations is measured by radioimmunoassay (RIA) using a commercially available kit. Both formulations are expected to produce measurable amounts of sCT in the blood, the maximum concentration of sCT in the blood of dogs given F1 is expected to be in the range of 0.5 to 6.0 ng/ml, whereas the maximum concentration of sCT in dogs given F2 is expected to be at least 1 to 12 ng/ml.

The bioavailability of sCT in dogs given F1 is expected to be approximately 1%, whereas the bioavailability of sCT in dogs given F2 is expected to be at least 1.2%. The in vivo cleavage of MT from sCT in dogs given F2 is proven by applying samples of plasma from dogs given F1 and F2 to an HPLC column and collecting the effluent in plastic tubes. The solvent in the tubes is removed under vacuum and analyzed for the presence of sCT by RIA. The in vivo cleavage of MT3sCT01 is established by showing that the retention time of sCT in the plasma from dogs given F2 is the same as the retention time of sCT in the plasma of dogs given F1.

Although the present invention has been described in relation to particular embodiments thereof, many other variations and modifications and other uses will become apparent to those skilled in the art. The present invention therefore is not limited by the specific disclosure herein, but only by the claims.

What is claimed is:

1. A pharmaceutical composition for oral delivery of a physiologically active peptide agent comprising:
   (A) a therapeutically effective amount of said active peptide linked to a membrane translocator, said membrane translocator possesses the capability of being at least partially cleaved from the active peptide in vivo by an enzyme;
   (B) at least one pharmaceutically acceptable pH-lowering agent and/or protease inhibitor; and
   (C) an acid resistant protective vehicle effective to transport said pharmaceutical composition through the stomach of a patient while preventing contact between said active peptide agent and stomach proteases.

2. The pharmaceutical composition of claim 1, wherein said membrane translocator comprises a molecule selected from the group consisting of peptide, fatty acid and bile acid.

3. The pharmaceutical composition of claim 2, wherein said peptide is a signal peptide.

4. The pharmaceutical composition of claim 1, wherein said membrane translocator comprises an amino acid sequence selected from at least one of the group consisting of all or part of kaposi fibroblast growth factor signal peptide, protein transduction domain of HIV TAT protein, human integrin β2 signal sequence, HSV-1 VP22 protein and OmpA signal peptide.

5. The pharmaceutical composition of claim 1, wherein said pH-lowering agent is present in said pharmaceutical composition in a quantity which, if said composition were added to ten milliliters of 0.1M aqueous sodium bicarbonate solution, would be sufficient to lower the pH of said solution to no higher than 5.5.

6. The pharmaceutical composition of claim 1, wherein said pH-lowering agent is present in a quantity which, if said composition were added to ten milliliters of 0.1M aqueous sodium bicarbonate solution, would be sufficient to lower the pH of said solution to no higher than 3.5.

7. The pharmaceutical composition of claim 1, wherein said protease inhibitor is a stomach and/or intestine protease inhibitor.

8. The pharmaceutical composition of claim 1, wherein said protease inhibitor inhibits an enzyme selected from the group consisting of pepsin, trypsin, chymotrypsin, elastase, kallikrein and carboxypeptidase.

9. The pharmaceutical composition of claim 1, wherein said in vivo enzyme is selected from the group consisting of caspase-1, caspase-3, proprotein convertase 1, proprotein convertase 2, proprotein convertase 4, proprotein convertase 4 PACE 4, prolyl oligopeptidase, endothelin cleaving enzyme, dipeptidyl-peptidase IV, signal peptidase, neprilysin, renin and esterase.

10. The pharmaceutical composition of claim 1, wherein said protective vehicle is present at a weight which is no more than 30% of the weight of the remainder of said pharmaceutical composition.

11. The pharmaceutical composition of claim 1, wherein said protective vehicle is present at a weight which is no more than 20% of the weight of the remainder of said pharmaceutical composition.

12. The pharmaceutical composition of claim 1, wherein said protective vehicle is present at a weight which is between 10% and 20% of the weight of the remainder of said pharmaceutical composition.

13. The pharmaceutical composition of claim 1, wherein said protective vehicle is sufficient to prevent breakdown of said pharmaceutical composition in 0.1N HCl for at least two hours, yet permits complete release of all contents of said pharmaceutical composition within 45 minutes after pH is increased to 6.3 in a dissolution bath in which said composition is rotating at 100 revolutions per minute.

14. The pharmaceutical composition of claim 1 further containing at least one absorption enhancer effective to promote bioavailability of said active agent.

15. The pharmaceutical composition of claim 14, wherein said absorption enhancer is a surface active agent.

16. The pharmaceutical composition of claim 15, wherein said surface active agent is absorbable or biodegradable.

17. The pharmaceutical composition of claim 16, wherein said surface active agent is selected from the group consisting of acylcarnitines, phospholipids and bile acids.

18. The pharmaceutical composition of claim 17, wherein said enhancer is an acyl carnitine.

19. The pharmaceutical composition of claim 18, further including a sucrose ester.

20. The pharmaceutical composition of claim 14, wherein said absorption enhancer is a surface active agent selected from the group consisting of (i) an anionic agent that is a cholesterol derivative, (ii) a mixture of a negative charge neutralizer and an anionic surface active agent, (iii) non-ionic surface active agents, and (iv) cationic surface active agents.

21. The pharmaceutical composition of claim 14, wherein said absorption enhancer is selected from the group consisting of a cationic surfactant and an anionic surfactant that is a cholesterol derivative.

22. The pharmaceutical composition of claim 14, wherein said pharmaceutical composition includes at least two absorption enhancers, one of which is a cationic surface active agent, and another of which is an anionic surface active agent that is a cholesterol derivative.

23. The pharmaceutical composition of claim 22, wherein said anionic surface active agent is an acid-soluble bile acid.

24. The pharmaceutical composition of claim 1, further comprising an amount of a second peptide that is not a physiologically active peptide effective to enhance bioavailability of said peptide active agent.

25. The pharmaceutical composition of claim 1, further comprising a water soluble barrier that separates said pH-lowering agent from said protective vehicle.

26. A pharmaceutical composition of claim 1, wherein said composition includes at least one pH-lowering agent that has a pKa no higher than 4.2.

27. The pharmaceutical composition of claim 1, wherein at least one pH-lowering agent has a solubility in water of at least 30 grams per 100 milliliters of water at room temperature.

28. The pharmaceutical composition of claim 1, wherein all ingredients other than said protective vehicle are uniformly dispersed.

29. The pharmaceutical composition of claim 28, wherein said pharmaceutical composition comprises granules containing a pharmaceutical binder and, uniformly dispersed in said binder, said pH-lowering agent, said absorption enhancer and said peptide active agent.

30. The pharmaceutical composition of claim 14, wherein said composition is a solid dosage form wherein a weight ratio of said pH-lowering agent to said absorption enhancer is between 3:1 and 20:1.

31. The pharmaceutical composition of claim 14, wherein said composition is a solid dosage form wherein the weight ratio of said pH-lowering agent to said absorption enhancer is between 5:1 and 10:1.

32. The pharmaceutical composition of claim 1, wherein said pH-lowering agent is selected from the group consisting of citric acid, tartaric acid and an acid salt of an amino acid.

33. The pharmaceutical composition of claim 1, wherein said pH-lowering agent is present in an amount not less than 300 milligrams.

34. The pharmaceutical composition of claim 33, wherein said pH-lowering agent is present in an amount which is not less than 400 milligrams.

35. The pharmaceutical composition of claim 1, wherein said peptide agent is human glucagon-like peptide 1 or analog thereof.

36. The pharmaceutical composition of claim 1, wherein said peptide agent is salmon calcitonin.

37. The pharmaceutical composition of claim 1, wherein said peptide agent is insulin.

38. The pharmaceutical composition of claim 1, wherein said peptide agent is human parathyroid hormone or analog thereof.

39. The pharmaceutical composition of claim 1, wherein said protective vehicle is a viscous protective syrup.

40. The pharmaceutical composition of claim 36, wherein the weight ratio of said pH-lowering agent to said salmon calcitonin is at least 200:1.

41. The pharmaceutical composition of claim 36, wherein the weight ratio of said pH-lowering agent to said salmon calcitonin is at least 800:1.

42. The pharmaceutical composition of claim 36, wherein the weight ratio of said pH-lowering agent to said salmon calcitonin is at least 2000:1.

43. The pharmaceutical composition of claim 32, wherein a water soluble barrier separates said pH-lowering agent from said protective vehicle.

44. The pharmaceutical composition of claim 36, wherein said enteric coating is present at a weight which is no more than 30% of the weight of the remainder of said pharmaceutical composition excluding said protective vehicle.

45. A method for enhancing the bioavailability of an orally delivered physiologically active peptide agent comprising:
   (A) linking said peptide agent to a membrane translocator that possesses the capability of being at least partially cleaved in vivo by an enzyme; and
   (B) selectively releasing said peptide active agent linked to said membrane translocator, together with at least one pH-lowering agent and/or protease inhibitor into a patient's intestine following passage of said peptide active agent, pH-lowering agent and/or protease inhibitor through said patient's mouth and stomach under protection of an acid resistant protective vehicle which substantially prevents contact between stomach proteases and said peptide agent.

46. The method of claim 45, wherein said membrane translocator comprises a molecule selected from the group consisting of signal peptide, fatty acid and bile acid.

47. The method of claim 45, wherein said membrane translocator comprises an amino acid sequence selected from the group consisting of all or part of kaposi fibroblast growth factor signal peptide, protein transduction domain of HIV TAT protein, human integrin β2 signal sequence and HSV-1 VP22 protein.

48. The method of claim 45, wherein said pH-lowering agent is present in said pharmaceutical composition in a quantity which, if said composition were added to ten milliliters of 0.1M aqueous sodium bicarbonate solution, would be sufficient to lower the pH of said solution to no higher than 5.5.

49. The method of claim 45, wherein said pH-lowering compound is present in a quantity which, if said composition were added to ten milliliters of 0.1M aqueous sodium bicarbonate solution, would be sufficient to lower the pH of said solution to no higher than 3.5.

50. The method of claim 45, wherein said protease inhibitor is a stomach and/or intestine protease inhibitor.

51. The method of claim 45, wherein said protease inhibitor inhibits an enzyme selected from the group consisting of pepsin, trypsin, chymotrypsin, elastase, kallikrein and carboxypeptidase.

52. The method of claim 45, wherein said in vivo enzyme is selected from the group consisting of caspase-1, caspase-3, proprotein convertase 1, proprotein convertase 2, proprotein convertase 4, proprotein convertase 4 PACE 4, prolyl oligopeptidase, endothelin cleaving enzyme, dipeptidyl-peptidase IV, signal peptidase, neprilysin, renin and esterase.

53. The method of claim 45, wherein the release of said peptide active agent into a patient's intestine is carried out in the presence of at least one absorption enhancer effective to promote bioavailability of said peptide active agent.

54. The method of claim 45, wherein said peptide agent is salmon calcitonin.

55. The method of claim 54, wherein the weight ratio of said pH-lowering agent to said salmon calcitonin is at least 800:1.

56. The method of claim 54, wherein the weight ratio of said pH-lowering agent to said salmon calcitonin is at least 200:1.

57. The method of claim 54, wherein the weight ratio of said pH-lowering agent to said salmon calcitonin is at least 2000:1.

* * * * *